(12) United States Patent
Euliano et al.

(10) Patent No.: US 8,211,015 B2
(45) Date of Patent: *Jul. 3, 2012

(54) OBSTETRIC ANALGESIA SYSTEM

(75) Inventors: Tammy Y. Euliano, Gainesville, FL (US); Neil Russell Euliano, II, Gainesville, FL (US); Jose C. Principe, Gainesville, FL (US); Dorothee Marossero, Gainesville, FL (US)

(73) Assignees: University of Florida Research Foundation, Inc., Gainesville, FL (US); Convergent Engineering, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/986,520

(22) Filed: Jan. 7, 2011

(65) Prior Publication Data

US 2011/0192398 A1   Aug. 11, 2011

Related U.S. Application Data

(63) Continuation of application No. 11/627,541, filed on Jan. 26, 2007, now Pat. No. 7,942,818.

(60) Provisional application No. 60/764,077, filed on Feb. 1, 2006, provisional application No. 60/787,336, filed on Mar. 30, 2006.

(51) Int. Cl.
*A61B 5/00* (2006.01)

(52) U.S. Cl. ............ 600/304; 600/511; 600/26; 600/27; 600/28; 607/46

(58) Field of Classification Search .............. 600/26–28, 600/304, 511; 607/46
See application file for complete search history.

(56) References Cited

U.S. PATENT DOCUMENTS

| | | | |
|---|---|---|---|
| 5,025,787 A | 6/1991 | Sutherland et al. | |
| 5,372,139 A | 12/1994 | Holls et al. | |
| 5,596,993 A * | 1/1997 | Oriol et al. | 600/511 |
| 6,723,077 B2 | 4/2004 | Pickup et al. | |
| 6,745,764 B2 | 6/2004 | Hickle | |
| 7,333,850 B2 | 2/2008 | Marossero et al. | |
| 2001/0025156 A1 | 9/2001 | Bui et al. | |
| 2002/0013357 A1 | 1/2002 | Nadkarni et al. | |
| 2004/0243015 A1 | 12/2004 | Smith et al. | |
| 2005/0267377 A1 * | 12/2005 | Marossero et al. | 600/511 |
| 2005/0277912 A1 * | 12/2005 | John | 604/890.1 |
| 2006/0189882 A1 | 8/2006 | Thomas | |
| 2007/0066908 A1 | 3/2007 | Graupe et al. | |

(Continued)

FOREIGN PATENT DOCUMENTS

EP   1 844 706   10/2007

(Continued)

OTHER PUBLICATIONS

Bell, A. et al., "An Information-Maximization Approach to Blind Separation and Blind Deconvolution," *Neural Computation*, 1995, vol. 7, pp. 1129-1159.

(Continued)

*Primary Examiner* — Patricia Mallari
*Assistant Examiner* — Michael D'Angelo
(74) *Attorney, Agent, or Firm* — Saliwanchik, Lloyd & Saliwanchik

(57) ABSTRACT

The present invention relates to systems and methods for providing a short-acting analgesic agent in the management of pain during labor, wherein the system enables efficient, real-time prediction of contractions for the coordinated administration of analgesia such that the peak effectiveness of the analgesic coincides with the intermittent pain of labor.

22 Claims, 19 Drawing Sheets

U.S. PATENT DOCUMENTS

2007/0088226 A1     4/2007    Spence et al.

FOREIGN PATENT DOCUMENTS

| WO | WO 03/003905 | 1/2003 |
|---|---|---|
| WO | WO 03/028550 | 4/2003 |
| WO | WO 2004/084087 | 9/2004 |
| WO | WO 2005/039410 | 5/2005 |
| WO | WO 2005/052848 | 6/2005 |
| WO | WO 2009/013246 | 1/2009 |

OTHER PUBLICATIONS

Comon, P., "Independent Component Analysis, A New Concept?" *Signal Processing*, 1994, vol. 36, No. 3, pp. 287-314.

Garfield, R. E. et al., "Comparing uterine electromyography activity of antepartum patients versus term labor patients," *Am. J. Obstet. Gynecol.*, 2005, vol. 193, pp. 23-29.

Garfield, R. E. et al., "Use of uterine EMG and cervical LIF in monitoring pregnant patients," *BJOG*, 2005, vol. 112, pp. 103-108.

Hild II, K. et al., "Blind Source Separation Using Renyi's Mutual Information," *IEEE Signal Processing Letters*, Jun. 2001, vol. 8, No. 6, pp. 174-176.

Leman, H. et al., "Use of the electrohysterogram signal for characterization of contractions during pregnancy," *IEEE Trans. Biomed. Eng*, 1999, vol. 46, No. 10, pp. 1222-1229.

Maner, W. L. et al., "Predicting term and preterm delivery with transabdominal uterine electromyography," *Obstet. Gynecol.*, 2003, vol. 101, No. 6, pp. 1254-1260.

Mansour et al., "Uterine EMG spectral analysis and relationship to mechanical activity in pregnant monkeys," *Med. Biol. Eng Comput.*, Mar. 1996, p. 115.

Maul, H. et al., "Non-invasive transabdominal uterine electromyography correlates with the strength of intrauterine pressure and is predictive of labor and delivery," *J. Matern. Fetal Neonatal Med.*, 2004, vol. 15, pp. 297-301.

Verdenik, I. et al., "Uterine electrical activity as predictor of preterm birth in women with preterm contractions," *Eur. J. Obstet. Gynecol. Reprod. Biol.*, 2001, vol. 95, pp. 149-153.

Wolfs et al., "An electromyographic study of the human uterus during labor," *Obstet. Gynecol.*, Feb. 1971, vol. 37, No. 2, pp. 241-246.

Yang, H. et al., "Adaptive Online Learning Algorithms for Blind Separation: Maximum Entropy and Minimum Mutual Information," *Neural Computation*, 1997, vol. 9, pp. 1457-1482.

Arani et al. "Extracting uncontaminated neural signals using independent component analysis" University of California, San Diego, pp. 1-2.

Graupe et al. "Extraction of fetal ECG from maternal ECG early in pregnancy" *IJBEM*, 2005, vol. 7, No. 1, pp. 166-168.

He et al. "Application of ICA in removing artefacts from the ECG" *Dept. of Engineering Science*, University of Oxford, Oxford, UK, pp. 1-18.

Martens et al. "A robust fetal ECG detection method for abdominal recordings" *Physiological Measurement 28*, 2007, IOP Publishing Ltd., pp. 373-388.

\* cited by examiner

FIG. 11F

OBSTETRIC ANALGESIA SYSTEM

CROSS-REFERENCE TO A RELATED APPLICATION

This application is a continuation application of application Ser. No. 11/627,541, filed Jan. 26, 2007 now U.S. Pat. No. 7,942,818; which claims the benefit of U.S. provisional Application Ser. No. 60/764,077, filed on Feb. 1, 2006 and Ser. No. 60/787,336, filed on Mar. 30, 2006, all of which are hereby incorporated by reference in their entirety, including all figures, tables, and drawings.

GOVERNMENT SUPPORT

This invention was made with government support under NSF Grant Nos. 0239060 and 0128452 awarded by National Science Foundation. Accordingly, the government has certain rights in this invention.

FIELD OF THE INVENTION

The present invention relates to analgesic systems and methods, in particular, to systems and methods for providing a short-acting analgesic agent or method in the management of pain during labor, wherein the system enables efficient, real-time prediction of contractions for the administration of analgesia to coordinate with the intermittent pain of labor.

BACKGROUND OF THE INVENTION

According to the American Society of Anesthesiologist's Statement on Pain Relief During Labor, "Labor results in severe pain for many women. There is no circumstance where it is considered acceptable for a person to experience untreated severe pain, amenable to safe intervention, while under a physician's care. In the absence of a medical contraindication, maternal request is a sufficient medical indication for pain relief during labor. Pain management should be provided whenever medically indicated."While many non- and minimally-invasive, non-pharmacologic pain therapies have been promoted, including prepared childbirth, imagery, hypnosis, transcutaneous electrical nerve stimulation (TENS), intracutaneous sterile water injection, chiropractic, hydrotherapy, acupuncture, etc, many women opt for medications or methods to numb the nerves sensing labor pain. However the vast majority of patients prefer to remain awake and able to participate in the birth of their child. Any pain management technique must take into account both the safety of the mother, and of the fetus. Agents that cross into the maternal brain for effect (e.g. sedatives and most i.v. analgesics) can similarly cross the placental barrier and reach the fetus.

The first stage of labor is characterized by brief (1-2 minute) intervals of severe pain, followed by moments of relative comfort. Current pharmacologic options for labor analgesia during this stage include i.v. opioids, paracervical nerve blocks, inhalational analgesia (much more common outside the United States), and neuraxial anesthesia (spinal or epidural). There are advantages and disadvantages to each.

An array of opioids has been studied in labor, but there is little scientific basis to suggest an advantage of one drug over another in the obstetric setting. Worldwide, intravenous opioids are the most common labor analgesic. Opioids share side effects including nausea/vomiting, pruritus, sedation, changes in heart rate (both maternal and fetal) and, of most concern, respiratory depression. Moreover, due to their lipophilicity, all opioids readily cross the placenta, entering fetal circulation. Thus, i.v. opioids have the potential for adverse neonatal effects (e.g., decreased beat-to-beat variability in the fetal heart rate pre-delivery, and neonatal respiratory depression). Further, the efficacy of opioids is limited due to the character of labor pain; for example, doses of i.v. opioids sufficient to provide analgesia during contractions cause unacceptable side effects between contractions.

Paracervical blocks require the administration of local anesthetics into the cervix where the sensory nerves from the uterus exit. While this provides excellent analgesia for the first stage of labor, the proximity of the injection site to the uterine arteries causes an unacceptable frequency of fetal bradycardia. For this reason, paracervical blocks rarely are used in the United States.

Pudendal blocks provide analgesia for the second stage of labor and are relatively safe. The most difficult issue is timing, in that the pain relief is only of the sacral nerves, and is therefore not useful until the fetal head is low. However, at that time, it is often difficult to access the anatomic location in the pelvis for appropriate placement of the block.

Modern inhalation analgesia consists almost exclusively of nitrous oxide. Though rarely used in the United States, various concentrations of nitrous oxide in oxygen are routinely used to relieve labor pain elsewhere, either alone or as an adjunct to other analgesic techniques. In most cases the patient self-administers a set concentration (30-70%) of nitrous oxide as she senses the onset of a contraction. Limitations include hypoxia, pollution of the local environment, occupational exposure, and the timing of nitrous oxide inhalation relative to the onset of contraction-induced pain.

Epidural analgesia involves the placement of local anesthetic and/or opioids into the epidural space. While an epidural usually provides superb analgesia, its placement is objectionable to some patients, contraindicated in others, and may be unavailable at many small hospitals. Usually a catheter is left in the space for continuous infusion of analgesics. This method of analgesia is more effective than i.v. opioids and results in less maternal and neonatal depression because of lower blood opioid levels. Furthermore, should the patient require a cesarean delivery, the epidural catheter can be used for surgical anesthesia. There are, however, risks associated with the placement of an epidural including headache, bleeding, infection, and nerve damage. Furthermore, epidural analgesia is contraindicated in some conditions (hemorrhage, coagulopathy), not offered at many hospitals, particularly smaller facilities, and is rare in many parts of the world.

While neuraxial analgesia provides superior pain relief, an effective alternative is necessary for those patients in whom neuraxial analgesia is either contraindicated or objectionable. Currently regimens utilizing morphine or meperidine provide more sedation than actual analgesia (Olofsson C et al., "Lack of analgesic effect of systemically administered morphine or pethidine on labour pain," Br. J. Obstet. Gynaecol., 968-72 (1996)), and the same may be true for remifentanil, particularly as labor progresses and pain increases. However, despite pain scores that remain in the moderate range (6-8 cm), patients consistently report improved satisfaction with remifentanil versus meperidine.

Remifentanil hydrochloride is an ultra-short acting, phenylpiperidine μ-specific opioid receptor agonist. In the non-obstetric population, remifentanil has a rapid onset of peak effect (blood-brain equilibration time, 1.2-1.4 min), short duration of action independent of infusion duration (context-sensitive half-life, 3 min), and rapid clearance (40 ml/kg/min). These qualities introduce the potential for titratability during labor. In fact, the physiologic changes of pregnancy (e.g. increased cardiac output) are expected to further speed the onset, while the clearance rate is increased as well (Kan RE et al., "Intravenous remifentanil: placental transfer, maternal and neonatal effects," *Anesthesiology*, 1467-74 (1998)). Remifentanil's unique pharmacokinetic profile is attributed to rapid metabolism by nonspecific esterases in blood and tissues.

Unfortunately, side effects of remifentanil are similar to those of other opioids (such as nausea, sedation, respiratory depression), the only difference being that with remifentanil, the side effects rapidly resolve with dose reduction or temporary discontinuation of the agent. Sometimes, to ensure adequate analgesia during a contraction, continuous infusion of remifentanil provided, which produces unacceptable levels of sedation between contractions. Attempts to administer remifentanil by PCA (patient-controlled analgesia) have been complicated by the delay in the onset of analgesia from (1) maternal sensation of a contraction, to (2) pressing the PCA button, to (3) bolus administration, to (4) clinical effect. Accordingly, some lead-time is needed to start the bolus such that the analgesia will be effective at the time of contraction. Unfortunately, there are no methods available to provide the lead-time necessary to initiate administration of the analgesia to peak with a contraction.

As noted herein, current forms of analgesia do not effectively address pain management during labor for those who cannot or choose not to receive a neuraxial block. Accordingly, a labor analgesia system is needed that can effectively manage pain during labor via analgesic administration that matches the timing and intensity of contraction-induced pain.

BRIEF SUMMARY OF THE INVENTION

The subject invention relates to an obstetric analgesia system that enables administration of an analgesic based on the timing and/or intensity of contraction-induced pain so that the analgesic effect is coincident with contraction pain. According to the subject invention, the analgesic may be a drug that is highly titratable, with a rapid and predictable onset, and a short duration of bio-activity. In a preferred embodiment, the obstetric analgesia system of the invention utilizes the analgesic Remifentanil (GlaxoWellcome, North Carolina).

In one embodiment, an obstetric analgesia system is provided for the administration of short acting intravenous, transdermal, transmucosal, or intramuscular analgesia, that supplies improved pain relief, timed to contractions, yet is safe for both mother and fetus/newborn. In other embodiments, an obstetric analgesia system is provided for the administration of inhalational analgesia, or electrical stimulation (e.g. transcutaneous electrical nerve stimulation (TENS) unit) or other method which impedes pain sensation, which is delivered/applied sufficiently early to the patient to have effect during the painful portion of a labor contraction.

According to the subject invention, the obstetric analgesia system provides novel methods for analyzing uterine activity in the prediction of labor contractions to establish time of contraction pain and optimal time of analgesic administration. In a related embodiment, the obstetric analgesia system monitors the time of contraction and, based on the monitored contraction activity, communicates to the user specific data regarding the contraction. Contemplated data communicated to the user include, but are not limited to, time relative to the contraction and intensity of the contraction.

Currently available technologies that can analyze and monitor uterine activity include, but are not limited to, the tocodynamometer, intrauterine pressure catheter (IUPC), and uterine electromyogram (EMG; or also known as the electrohysterogram; EHG). According to the subject invention, EHG activity, when detected reliably at its onset, is an effective precursor for identifying the onset of contractions for use in the coordinated delivery of an analgesic so that the analgesic's pain-relieving ability coincides with contraction-induced pain.

In one embodiment, the maternal-fetal monitoring system as described in U.S. patent application Ser. No. 10/857,107, filed May 28, 2004, which is incorporated by reference in its entirety, is used according to the subject invention to predict the onset of contractions and, in certain instances, the onset of contraction-induced pain. The maternal-fetal monitoring system monitors electrical activity of the uterus (electrohysterogram EHG) via maternal abdominal electrodes. In most cases, this electrical activity precedes the onset of the contraction. From the EHG activity, the subject obstetric analgesia system predicts the onset of a contraction with sufficient lead-time to enable coincidental administration of an analgesic (such as remifentanil or nitrous oxide) to obtain appropriate analgesic blood levels to effectively manage the pain that is induced by episodic contractions. The subject invention's method for predicting the onset of contractions and, in certain instances, the onset of contraction-induced pain, can be used with any patient experiencing labor; including patients that are underweight or morbidly obese.

In another embodiment of the invention, an obstetric analgesia system is provided that creates a reliable contraction signal that is communicated to the user, where the contraction signal informs the user of the onset of a contraction 10-20 seconds earlier than traditional uterine activity monitoring. In a related embodiment, advanced contraction signal processing and neural network detection is applied to data regarding uterine muscle activity that is collected from an array of electrodes placed on the maternal abdomen. According to the subject invention, uterine muscle activity appears up to 10-20 seconds before significant pressure increases in the uterus.

Accordingly, in a related embodiment of the invention, the obstetric analgesia system can provide a signal that can be used by the user to deliver a short-acting analgesic to the patient in advance of the contraction so that the pain-relieving ability of the analgesia peaks with the contraction. For example, the obstetric analgesia system can provide an audible or visible warning signal to notify the caregiver to provide analgesia to the patient so that the pain-relieving ability of the analgesic coincides with the onset of contraction-induced pain.

In another related embodiment, the subject analgesia system provides a signal that can be used by the patient to trigger patient controlled delivery of an analgesic. Accordingly, the subject obstetric analgesia system includes a PCA feature for patient controlled delivery of analgesia based on the signal given regarding the onset of a contraction.

In another embodiment of the invention, an obstetric analgesia system is provided that has an automated analgesic delivery feature for automatic delivery of the analgesic and/or adaptive alteration of the analgesic concentration based on monitored contraction activity (e.g., via monitored EHG activity). In a related embodiment of the invention, the obstetric analgesia system can determine the extent of contraction-induced pain, and based on this data, alter the analgesic concentration. This "extent of contraction-induced pain" may be determined from either (1) the current EHG; (2) the time history of the EHG; (3) via patient input into the system, or through some combination of (1)-(3) above, whereby the system learns the patient's demands relative to the contraction intensity.

Another embodiment of the invention includes using IUPC, tocodynamometer, or other uterine activity monitoring methods along with a time history of the uterine activity to implement the system. Additionally, the standard uterine activity monitoring methods could be used in conjunction with the EHG method for better performance.

In yet another embodiment, the subject invention provides additional features to monitor clinical data regarding patient (maternal and/or fetal) response to the analgesic. For example, certain embodiments of the invention include a pulse oximeter and/or respiratory rate monitoring apparatus that enables the user (e.g., caregiver) to monitor and effectively treat any respiratory depression associated with the delivery of the analgesic (i.e., disable the obstetric analgesia system and/or increase patient inspired oxygen concentration). In a related embodiment, the obstetric analgesia system includes means for maternal hemodynamic and fetal heart rate analysis.

In certain embodiments, the obstetric analgesia system includes an automated shut-off feature for shutting off the delivery of analgesia should the patient exhibit detrimental effects from the analgesia.

In other embodiments, the obstetric analgesia system includes automated features for addressing specific detrimental effects from the analgesia. For example, the obstetric analgesia system of the invention can include a means for increasing inspired oxygen concentration (e.g., via nasal canula or facemask).

In a preferred embodiment, a novel obstetric analgesia system is provided that automatically delivers boluses of remifentanil (or any future short-acting opioid or other analgesic) in advance of EHG-detected contractions. The system preferably accepts patient input to titrate the bolus dose, and includes a respiratory monitor such as the pulse oximeter to monitor the patient's oxygen saturation to ensure safety. In a related embodiment, the obstetric analgesia system preferably controls the delivery of nitrous oxide (as opposed to or in addition to remifentanil), while continuously monitoring patient clinical status with pulse oximetry. In another related embodiment, the obstetric analgesia system preferably controls a transdermal, transmucosal or intramuscular administration system.

BRIEF DESCRIPTION OF THE FIGURES

Figure 11F:
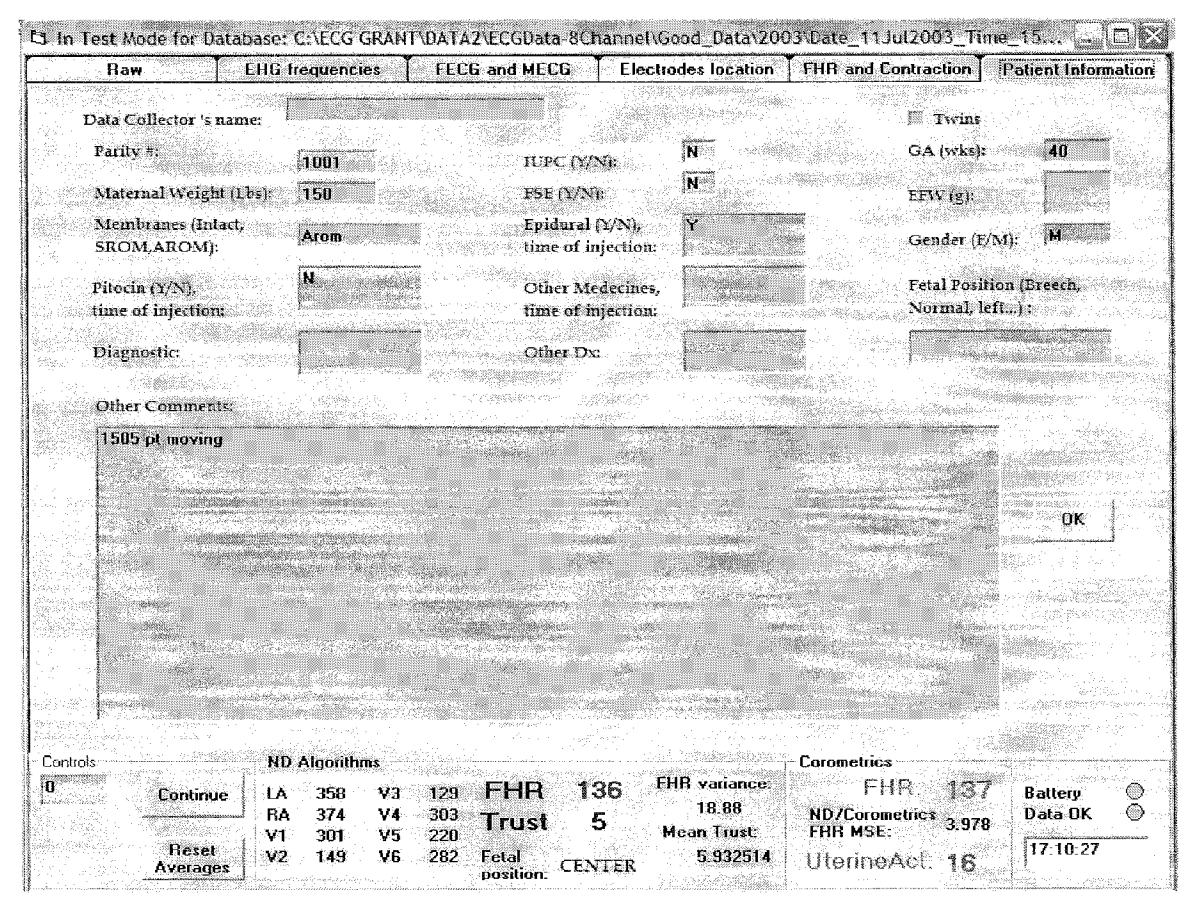

FIGS. 11A-F are examples of computer user-interface pages presented to a user in accordance with the subject invention.

DETAILED DESCRIPTION OF THE INVENTION

Figure 1:
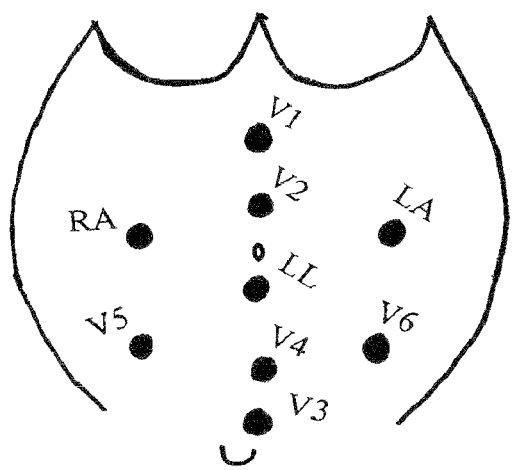
FIG. 1 illustrates an array of electrodes placed over the maternal abdomen for use in acquiring clinical data regarding uterine activity.

The present invention provides novel analgesic systems and methods for managing pain during labor. According to the present systems and methods, clinical contraction data (and subsequent contraction-induced pain) are monitored for use in coordinating delivery of pain management means methods to have effect that is coincident with contraction pain.

In accordance with one embodiment of the invention, an obstetric analgesic system is provided that comprises (1) a means for extracting clinical data for use in establishing contraction data and/or uterine activity; (2) a means for establishing contraction data and/or uterine activity for use in coordinating analgesic delivery; and (3) a means for delivering an analgesic to an obstetric patient in need of pain management during labor timed to episodic contraction-induced pain.

In operation, a clinical data extraction means is used to obtain clinically relevant data regarding maternal and/or fetal condition. Preferably, the clinical data extraction means transmits the clinical data to a means for establishing contraction data. The means for establishing contraction data contains algorithms for determining data such as contraction onset, contraction frequency, contraction duration, contraction intensity, time history of contractions, and the like. The contraction data is then used to determine the time needed to deliver an analgesic so that the effectiveness of the analgesic coincides with contraction-induced pain. Based on the determined time for analgesic delivery, the analgesic delivery means is activated to deliver the analgesic to the obstetric patient.

The embodiments described herein are applicable to any female patient experiencing labor pains. In certain embodiments, the present invention is particularly advantageous for use with pregnant patients diagnosed as morbidly obese or underweight. As understood by the skilled artisan, morbid obesity refers to patients who are 50-100%—or 100 pounds above—their ideal body weight (or, alternatively, a patient who has a BMI (body mass index) value greater than 39). An underweight patient is one whose weight is less than normal, healthy, or required.

It should be understood that modifications of the obstetric analgesic system described herein may be made in order to supply other pain management medications. Such modifications will be readily apparent, from the description set forth herein, to one of ordinary skill in the design of analgesic systems.

Extraction of Clinical Data

There are various technologies currently available to the clinician for extracting clinical data relating to maternal and/or fetal condition that can be used in accordance with the present invention to establish contraction data (such as contraction onset, contraction frequency, contraction duration, and the like). Such technologies include, but are not limited to, maternal sensation, caregiver palpation of the uterus, the tocodynamometer, intrauterine pressure catheter (IUPC), electrohysterography (uterine EMG), and magnetohysterography.

In one embodiment, detection of intrauterine contractions for use with the obstetric analgesic system of the invention can be performed using a conventional tocodynamometer or tocotransducer. Tocotransducers can sense uterine activity externally and non-invasively by measuring the hardness of the abdominal wall. They are held in place by a belt-like device which holds the sensor in the vicinity of the fundus (the top of the uterus).

In another embodiment, an IUPC is used with the obstetric analgesic system of the invention to extract contraction data for use in coordinating analgesic delivery such that analgesic effectiveness coincides with episodic contraction-induced pain. An IUPC is placed into the uterus, alongside the fetus, to measure the pressure generated by uterine contractions. Based on such measurements, the contraction establishing means of the invention can extract contraction data such as contraction onset, contraction frequency, contraction duration, contraction intensity, time history of contractions, and the like, that is useful in establishing an appropriate time and strength for analgesic delivery to manage contraction pain.

The uterine electrohysterogram has been investigated for more than 50 years. Recently there has been renewed interest in this signal for predicting preterm delivery (Leman H et al., "Use of the electrohysterogram signal for characterization of contractions during pregnancy," *IEEE Trans. Biomed. Eng*, 1222-9 (1999); Maner W L et al., "Predicting term and preterm delivery with transabdominal uterine electromyography," *Obstet. Gynecol.*, 1254-60 (2003); and Verdenik I et al., "Uterine electrical activity as predictor of preterm birth in women with preterm contractions," *Eur. J. Obstet. Gynecol. Reprod. Biol.*, 149-53 (2001)) and onset of labor (Garfield RE et al., "Use of uterine EMG and cervical LIF in monitoring pregnant patients," *BJOG*, 103-8 (2005)), as well as for replacement of the intrauterine pressure catheter (IUPC) (Maul H et al., "Non-invasive transabdominal uterine electromyography correlates with the strength of intrauterine pressure and is predictive of labor and delivery," *J. Matern. Fetal Neonatal Med.*, 297-301 (2004)). These investigations have focused on the power density spectrum (PDS) peak frequency (Garfield RE et al., "Comparing uterine electromyography activity of antepartum patients versus term labor patients," *Am. J. Obstet. Gynecol.*, 23-9 (2005); Garfield RE et al. *BJOG*, 103-8 (2005); Maner W L et al., *Obstet. Gynecol.*, 1254-60 (2003)), the RMS (root mean square) and median frequency of uterine electrical activity (Verdenik I et al., *Eur. J. Obstet. Gynecol. Reprod. Biol.*, 149-53 (2001)), evaluation of power in various frequency bands (Leman H et al., *IEEE Trans. Biomed. Eng*, 1222-9 (1999)), or total "burst energy" (PDS×burst duration) (Maul H et al., *J. Matern. Fetal Neonatal Med.*, 297-301 (2004)).

With specific reference to contraction onset, Wolfs et al. ("An electromyographic study of the human uterus during labor," *Obstet. Gynecol.* 241-6 (1971)), using intrauterine electrodes, found electrohysterogram (EHG) activity consistently begins earlier than mechanical activity (IUP). They reported that the latency between these appears to diminish over the course of labor, which they attribute to increased conduction velocity. While they did not give statistics on this latency, in one diagram the EHG anticipates the IUP change by almost 20 seconds at complete cervical dilation.

In cynomolgus monkeys, Mansour et al. ("Uterine EMG spectral analysis and relationship to mechanical activity in pregnant monkeys," *Med. Biol. Eng Comput.*, 115-21 (1996)) looked at both internal and external EHG recordings and found excellent correlation between the two. They report a latency of 1 to 13 seconds (average appears to be 8-10 sec) between onset of electrical versus mechanical activity.

Uterine contractions are the result of the coordinated actions of individual myometrial cells. At the cellular level, the contractions are triggered by a voltage signal called an action potential. During pregnancy, cellular electrical connectivity increases such that the action potential propagates to produce a coordinated contraction involving the entire uterus. The action potential during a uterine contraction can be measured with electrodes placed on the maternal abdomen resulting in a uterine EMG signal (hereinafter referred to as "EHG": electrohysterogram). Specifically, the EHG signal can be processed to produce a signal that is similar to the standard uterine activity signal from the tocodynamometer or IUPC. The EHG provides contraction frequency, intensity, and duration information.

Accordingly, in one embodiment, multiple electrode sensors are placed on the patient's abdomen to acquire uterine EMG data for use in extracting data regarding EHG. Such EHG data is used in accordance with the present invention to establish patient contraction data during labor for use in coordinating analgesic delivery so that the effect of the analgesic coincides with contraction-induced pain.

More preferably, the systems and methods of the present invention utilizes a comprehensive, real-time EHG monitoring system, such as those disclosed in U.S. patent application Ser. No. 10/857,107, filed May 28, 2004, to extract EHG data for use in establishing contraction clinical data. The EHG monitoring system preferably performs any one or combination of the following steps: (1) using an independent component analysis algorithm (ICA) to separate maternal and fetal signals; (2) using signal processing means, as described below, for automatically determining the fetal and maternal clinical data; (3) using signal processing means for providing contraction information; and (4) using a neural network to track and present clinical estimates regarding contraction onset.

More preferably, an EHG monitor of the invention includes at least one sensor to acquire a uterine EMG signal and a signal processor for generating a signal representative of uterine activity (EHG). The EHG indicates uterine contraction data, such as contraction onset, contraction frequency, contraction duration, and contraction intensity.

Establishment of Contraction Data

The subject invention comprises a means for establishing contraction data based on extracted clinical data (such as EHG, intrauterine pressure, and/or tocodynamometer data). In a preferred embodiment, the means for establishing contraction data is a computing means for receiving and analyzing sensor input (e.g., from the electrodes, an IUPC, and/or a tocodynamometer) to accurately determine contraction onset, contraction frequency, contraction duration, contraction intensity, time of history of contractions, and the like. A graphical user interface can be included with the systems of the invention to display clinical data, contraction data, as well as enable user-interaction.

In one embodiment, the system of the invention further includes an intelligence system that can use the clinical data or contraction data generated by the computing means in offering clinical data for making decisions (i.e., interpret fetal or maternal well-being before and after analgesic administration, labor progress, etc.). In addition, the intelligence system can be provided in the analgesic system of the invention to enable real-time assistance in providing additional support in the management of pain (i.e., type of analgesic to administer, likelihood of delivery within a period of time, specific actions to take in case of detrimental maternal and/or fetal response to administered analgesic, etc.). An intelligence system of the subject invention can include, but is not limited to, artificial neural networks, fuzzy logic, evolutionary computation, knowledge-based systems, optimal linear or nonlinear filtering, and artificial intelligence.

In accordance with the subject invention, the computing means is preferably a digital signal processor, which can (1) automatically, accurately, and in real-time, extract maternal and fetal vital signals, including EHG signals, from sensor input; (2) assess the quality of clinical data (i.e., maternal and fetal vital signals) provided by the processor in view of environmental noise; and (3) determine, based on the clinical data, contraction onset, contraction frequency, contraction duration, contraction intensity, and the like.

Clinical signals (i.e., EHG signals, etc.) obtained in accordance with the subject invention are transmitted from the clinical data extraction means to a computing means for signal processing. The computing means can also be responsible for maintenance of acquired data as well as the maintenance of the obstetric analgesic system itself. The computing means can also detect and act upon user input via user interface means known to the skilled artisan (i.e., keyboard, interactive graphical monitors, pressure-sensitive hand-grip).

In one embodiment, the computing means further comprises means for storing and means for outputting processed data. The computing means includes any digital instrumentation capable of processing signals from the sensors of the invention (i.e., EHG signals). Such digital instrumentation, as understood by the skilled artisan, can process communicated signals by applying algorithm and filter operations. Preferably, the digital instrumentation is a microprocessor, a personal desktop computer, a laptop, and/or a portable palm device. The computing means can be general purpose or application specific.

The subject invention can be practiced in a variety of situations. The computing means can directly or remotely connect to a central office or health care center. In one embodiment, the subject invention is practiced directly in an office or hospital. In another embodiment, the subject invention is practiced in a remote setting, for example, personal residences, mobile clinics, vessels at sea, rural villages and towns without direct access to healthcare, and ambulances, wherein the patient is located some distance from the physician.

In a related embodiment, the computing means is a custom, portable design and can be carried or attached to the patient in a manner similar to other portable electronic devices such as a portable radio, or interwoven in the patient clothing as a wearable computer.

The computing means used in accordance with the subject invention can contain at least one user-interface device including, but not limited to, a keyboard, stylus, microphone, mouse, speaker, monitor, and printer. Additional user-interface devices contemplated herein include touch screens, strip recorders, joysticks, and rollerballs.

Preferably, the computing means comprises a central processing unit (CPU) having sufficient processing power to perform algorithm operations in accordance with the subject invention. The algorithm operations can be embodied in the form of computer processor usable media, such as floppy diskettes, CD-ROMS, zip drives, non-volatile memory, or any other computer-readable storage medium, wherein the computer program code is loaded into and executed by the computing means. Optionally, the operational algorithms of the subject invention can be programmed directly onto the CPU using any appropriate programming language, preferably using the C programming language.

In certain embodiments, the computing means comprises a memory capacity sufficiently large to perform algorithm operations in accordance with the subject invention. The memory capacity of the invention can support loading a computer program code via a computer-readable storage media, wherein the program contains the source code to perform the operational algorithms of the subject invention. Optionally, the memory capacity can support directly programming the CPU to perform the operational algorithms of the subject invention. A standard bus configuration can transmit data between the CPU, memory, ports and any communication devices.

In addition, as understood by the skilled artisan, the memory capacity of the computing means can be expanded with additional hardware and with saving data directly onto external mediums including, for example, without limitation, floppy diskettes, zip drives, non-volatile memory and CD-ROMs.

As described above, the computing means can include an A/D converter to translate analog signals into digital signals (i.e., an analog/digital card). The A/D converter preferably readies the signals for further processing according to the subject invention. Additional filtering steps may precede any algorithmic operations of the invention.

The computing means can further include the necessary hardware and software to convert processed signals into an output form readily accessible by the trained physician, nurse practitioner, midwife, or technician. For example, without limitation, an audio device in conjunction with audio speakers can convert and play an audio signal indicating a specified time to contraction onset, and/or a graphical interface can display EHG signals in a graphical form on a monitor and/or printer. Further, the computing means can also include the necessary software and hardware to receive, route and transfer data to a remote location.

Communication devices such as wireless interfaces, cable modems, satellite links, microwave relays, and traditional telephonic modems can transfer clinical data from a computing means to a healthcare provider via a network. Networks available for transmission of clinical data include, but are not limited to, local area networks, intranets and the open internet. A browser interface, for example, NETSCAPE NAVIGATOR or INTERNET EXPLORER, can be incorporated into communications software to view the transmitted data.

Advantageously, a browser or network interface is incorporated into the processing device to allow the user to view the processed data in a graphical user interface device, for example, a monitor. The results of algorithm operations (i.e., those used for determining contraction data) of the subject invention can be displayed in the form of the interactive graphics. The user, whether it be a physician, a nurse, a midwife, a technician, or a patient, can indicate the specific analgesic, or perhaps a combination of options for addressing contraction pain.

In one embodiment, a graphical representation of the contraction onset and duration is provided to enable the user to track when to deliver the analgesic. The system of the invention can accept patient-specific diagnoses/laboratory values and recommended drug titration based on known clearance issues (e.g., renal insufficiency). Patient history and physical data can also be used to determine the best possible parameters for the system (e.g., baseline drug flow, initial bolus volume, likelihood ratios for contraction timing prediction, etc.).

In certain embodiments of the invention, biofeedback for pushing effectiveness is included in the system to shorten the second stage of labor. Also, a methodology to titrate pitocin or other labor induction drugs can be included in the system of the invention.

Pain Assessment

In one embodiment, uni-dimensional and/or multi-dimensional scales are used to quantify pain for a variety of purposes including, but not limited to, (1) use in assessing the extent of contraction-induced pain and (2) use in assessing the efficacy of the analgesic delivered to the patient. Based on the assessment of (1) and/or (2), the subject obstetric analgesia system delivers an analgesic in accordance with the subject invention. Uni-dimensional and multi-dimensional scales are measurements employed by caregivers to extract subjective information about the extent of pain. Such scales utilize verbal (mild, moderate, severe) ratings, numerical (0-10) ratings, visual analog scales, and/or complex, pain diagnosis questionnaires to assess the extent of pain experienced by a patient.

In other embodiments, care givers use visual clues to quantify pain for the purposes identified above. Under this visual assessment method, the caregiver will commonly use a different visual analog scale (VAS), usually scored from 1 to 10, to rate a patient's pain intensity. In a typical scenario, the care giver will consider different clues to score the patient's pain intensity, such as facial expressions and cardio-respiratory function, in addition to patient statements of satisfaction.

Patient Controlled Administration

According to the subject invention, novel obstetric analgesic systems are provided that include a patient controlled analgesia (PCA) feature that enables the patient to self-administer pain medicine after a signal is communicated regarding the onset of a contraction (and subsequently, contraction-induced pain). Commercial PCA devices that can be incorporated into the systems and methods include devices such as the Atom PCA Pump 500, APII, Deltec CADD-PCA 5800, Sabratek 6060 and the Verifuse.

In a common form of PCA for use in the subject invention, the patient is provided with a mechanical apparatus comprised of a reservoir and a patient-operable pump. On patient demand, the pump dispenses incremental doses of pain medicine from the reservoir into the patient's intravenous (IV) system. The device may also comprise a lock-out interval feature that prevents patient remedication for a period of time so as to ensure against over-medication.

Pain Management

In certain embodiments of the invention, the computing means controls the time and delivery of one or more pain management means based on established contraction data. Contemplated pain management means include, but are not limited to: intravenous, subcutaneous, intramuscular, intraarticular, parenteral, peritoneal, intranasal, inhalational, oral, rectal, intravaginal, topical, nasal, ophthalmic, topical, transcutaneous, sublingual, epidural, intrathecal, delivery of pain medications (such as analgesics, anesthetics, sedatives, tranquilizers, or narcotic antagonist combinations) or electrical stimulation of the spinal nerves (such as with transcutaneous electrical nerve stimulation (TENS)).

Pain medications that can be automatically delivered based on established contraction data in accordance with the present invention include, but are not limited to, opioids, local anesthetics, barbiturates, phenothiazines, benzodiazepines, ketamine and mixed agents.

In certain embodiments, pain medications that cause loss of sensation are automatically delivered via any one of the following methods: local block, paracervical block, pudendal block, epidural anesthesia and analgesia, spinal anesthesia and analgesia, and inhalational anesthesia.

In one embodiment, after the computing means establishes contraction data relevant for use in coordinating analgesic delivery, a time for delivering an analgesic is established. At the established time, an audible, visual, or tactile signal warns the patient or clinician to administer an analgesic, or it is automatically supplied by the system of the invention to the patient so that the effectiveness of the analgesic coincides with the contraction-induced pain. The computing means also controls when to cease delivery of the analgesic to the patient so that the mother and/or fetus are not detrimentally affected.

In a related embodiment, the analgesic is administered via an automated I.V. delivery system that is in communication with the computing means. Based on the monitored contraction data, the computing means is able to communicate to the I.V. system the time for delivering an analgesic to the patient, where the I.V. system automatically delivers the analgesic based on the communicated times. Alternatively, the computing means regulates an I.V. system to ensure automated analgesic administration to the patient. One skilled in the art would readily recognize those I.V. systems applicable to the subject invention.

In certain embodiments of the invention, there are also provided sensors that monitor maternal and/or fetal condition during analgesic delivery. The sensors can communicate to the computing means any monitored distress in either the mother and/or fetus in relation to analgesic delivery. If there is any noted distress, the system of the invention can report the distress to the user and/or automatically activate those systems necessary to address the distress. For example, where maternal and/or fetal distress is identified, the system of the invention can automatically shut off analgesic delivery and sound an alarm to the user. Decreased maternal oxygen saturation or respiratory rate could be treated by reduced PCA dose and/or administration of supplemental oxygen. In the event of decreased fetal beat-to-beat variability, the system might temporarily reduce the opioid load to assess recovery of variability. Should it not recover in the expected timeframe, the user could be alerted to further assess fetal well being.

Additional Features—Software

Figure 7:
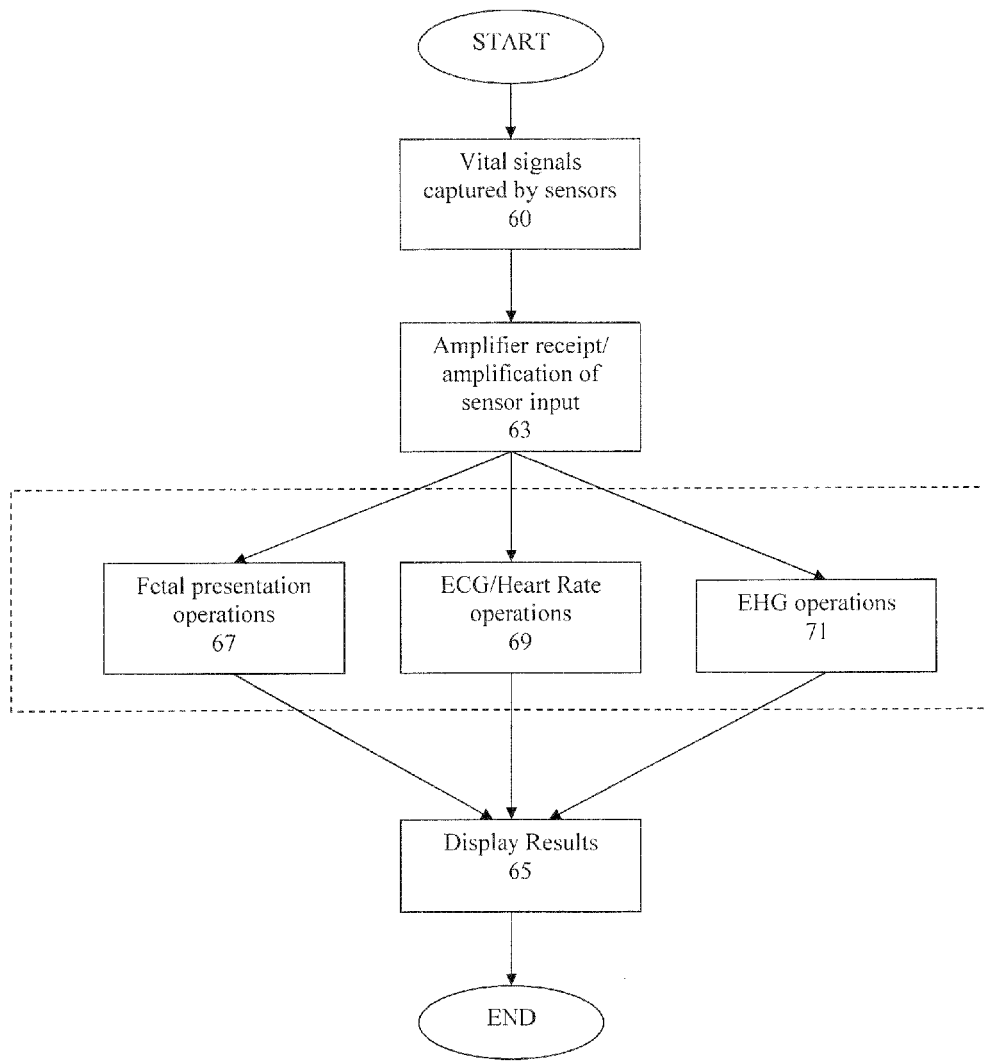
FIG. 7 is a flow diagram illustrating steps for operating a maternal-fetal monitoring system in accordance with the subject invention.

In certain embodiments, maternal-fetal monitoring can function in a real-time setting to continuously provide accurate clinical data to the user during analgesic delivery. In operation, as illustrated in FIG. 7, maternal-fetal vital signals (such as maternal and fetal heart rate, respiratory rate, ECG results, and EHG) are captured by sensors 60 (raw signals) and input to an amplifier (i.e., raw signals) 63. Amplifier output is subsequently communicated to a variety of operational algorithms 36 for processing vital signals into clinical data and subsequent presentation of clinical data to the user 65. Operational algorithms 36 can include, without limitation, fetal presentation operations 67, ECG/heart rate operations 69, and EHG operations 71.

In certain instances, prior to vital signal processing, signals received from an amplifier are communicated to filter operations for each sensor channel. Raw signals extracted by sensors of the invention are a mixture of several sources, namely maternal-fetal vitals signs (i.e., maternal ECG, fetal ECG, EMG signals) and noise. In a preferred embodiment, each sensor channel is communicated to a corresponding band pass filter operation, which is accomplished on a computing means. According to the subject invention, a computer processor is used for filter operations as well as other processing functions.

In accordance with the subject invention, the filtered signals are then followed by appropriate operations for obtaining desired clinical data (i.e., ECG results (maternal and fetal); EHG results; a value to aid the user in assessing the quality of clinical data). Contemplated operations include, but are not limited to, ICA operations, EHG extraction operations; quality ("trust") factor operations; Pan Tompkins analysis operations; maternal-fetal channel determination operations; ECG waveform reconstruction operations; and fetal presentation operations.

1—Independent Component Analysis (ICA) Operations

In accordance with the subject invention, filtered sensor output is communicated to ICA operators for each specific sensor channel used for ECG collection. ICA operators of the invention are preferably implemented in real time on a computing means (i.e., computer processor). The ICA operations place the filtered sensor output (i.e., mixture of signals from several sources—maternal, fetal and noise) into estimated independent components. In one embodiment, ICA operations are capable of calculating the estimated fetal ECG, estimated maternal ECG, and estimations of other noises in the filtered sensor output.

A variety of algorithms, known to the skilled artisan, are available for use in ICA operations of the subject invention. ICA (or blind source separation—BSS) algorithmic operations contemplated for use in ICA operations of the subject invention include, but are not limited to, Infomax ICA operations (Bell, A. and T. Sejnowski, "An Information-Maximization Approach to Blind Separation and Blind Deconvolution," *Neural Computation,* 7:1129-1159 (1995)); minimum mutual information operations (Comon, P., "Independent Component Analysis, A New Concept?" *Signal Processing,* 36(3):287-314 (1994)); maximum entropy and minimum mutual information operations (Yang, H. and S. Amari, "Adaptive Online Learning Algorithms for Blind Separation: Maximum Entropy and Minimum Mutual Information," *Neural Computation,* 9:1467-1482 (1997)); and Mermaid ICA operations (Hild, K. et al., "Blind Source Separation Using Renyi's Mutual Information," *IEEE Signal Processing Letters,* 8 (6):174-176 (2001)).

In a preferred embodiment, a Mermaid ICA algorithm is used in ICA operations of the subject invention. As known to the skilled artisan, a Mermaid ICA algorithm determines separate sources by minimizing the output mutual information. In one embodiment, the Mermaid ICA algorithm uses Renyi's entropy to estimate mutual information.

In certain embodiments, to simplify the computation of the gradient, a Mermaid ICA algorithm first projects the sources onto an orthonormal (whitened) space and then rotates these projections into a space of minimal mutual information. The projection is done with the well known Principal Component Analysis method. The rotation is done by adaptively updating the Givens angles. This update is done in an online manner by minimizing the mutual information between the outputs of the ICA algorithm.

The optimization steps are as follows: (1) initializing Givens angles (to all zeros or randomly); (2) computing the whitening matrix as prescribed using all samples in off-line separation/updating the whitening matrix using an adaptive principle components algorithm (PCA) in on-line; (3) using in off-line separation the batch gradient obtained by direct derivation of the optimal separation matrix parameters of the vector of Givens rotation angles, which is computed using all available samples; or, using in on-line separation, the stochastic gradient; and (4) updating the Givens rotation angles using the steepest descent. According to the subject invention, the use of a Mermaid ICA algorithm for ICA operations results in timely and accurate output.

2—Pan Tompkins Operations

In accordance with the subject invention, at the output of ICA operations, Pan Tompkins operations are performed on a computing means (i.e., computer processor). Pan Tompkins operations of the subject invention are based in part on a known, standard algorithm (the Pan Tompkins algorithm).

In one embodiment of the invention, the frequency bands of the Pan Tompkins algorithm are increased to higher frequencies and the lengths of the filters have been decreased. In a preferred embodiment, the following parameters of the standard Pan Tompkins algorithm are changed to fit the frequency range of fetal ECGs: (1) a band-pass filter; (2) a differentiation step (or function); and (3) a moving average step (function). More preferably, the parameters of the standard Pan Tompkins algorithm include the following: (1) a butterworth band-pass filter of order 6 and of pass band between 5 and 35 HZ is used; (2) a differentiation step of 5 point derivatives is used; (3) a moving average step following the squaring step uses a 20 point window.

The Pan Tompkins operations of the subject invention enable the detection of QRS complex peaks in the estimated maternal and fetal ECG signals (outputs of the ICA algorithm). In accordance with the subject invention, QRS complex location is used in calculating specific clinical data, namely fetal heart rate data.

In a related embodiment, Pan Tompkins operators perform computational analyses to provide clinical data such as RR intervals (defined herein as the time in seconds between 2 consecutive QRS peaks); instantaneous or beat to beat heart rate (HR)(60/RR); average HR, HR variance (which can be updated beat by beat); as well as estimated numbers of false positive and false negative QRS complexes. This clinical data (number of false positives, false negatives, etc.) can be input to maternal-fetal channel determination operators and/or quality ("trust") factor operators to determine which output channel is the fetal ECG and to determine the quality of the signal, respectively.

In accordance with the subject invention, preferably a false positive peak is estimated to be present when the RR interval between the previous peak and the present one is less than 70% of the average of the 5 previous RR intervals. Further, preferably a false negative according to the subject invention is estimated when the RR interval between the previous peak and the present one is greater than 130% of the average of the 5 previous RR intervals. Preferably, the average HR, HR variance, and number of false positive and false negative are calculated every 4 seconds.

3—Quality ("Trust") Factor Operations

In current monitoring systems, the signal separation performance cannot be directly measured because the actual original signals are not known. In contrast, the subject application enables determination of the quality of the separated signals (maternal versus fetal vital signals). In one embodiment of the invention, the quality of the ECG separation can be approximated by determining the properties of the ECG signals themselves. High quality ECG signals have high signal to noise ratios, clearly visible waveform characteristics typical of ECG waveforms, such as the P, Q, R, S, and T waves, and timing that is representative of the actual electromechanical beating of the heart. According to the subject invention, poor quality of signal separation indicates a great deal of noise whereas best quality of signal separation indicates any signal separation that is better than noise. For example, a quality of 0 is completely noise, a quality of 5 implies that the QRS waveform is clearly visible, repeatable, and much above the noise, and a quality of 7-10 implies that the P and T waves are visible.

The quality of the estimated fetal HR calculated from the fetal ECG and the quality of the fetal ECG signal itself, as extracted using the monitoring system of the subject invention, are directly related to the quality of the separation algorithm operations. There is currently no existing criterion for measuring the performance of separation algorithm (i.e., ICA or BSS) operations in environments where the mixing matrix is unknown (i.e., real data). According to the subject invention, a mechanism suitable for comparing the quality of separation algorithm operation performance on real data is based on an end-to-end system criterion (i.e., in terms of the real goals of the system).

Similarly, an EHG quality assessment (or trust factor) can be derived from the processed EHG signal based upon input variables corresponding to features that are characteristic of fetal or maternal EHG signals. In a preferred embodiment, the EHG quality assessment would be based on kurtosis, skewness, and the frequency components of the EHG signal. The kurtosis for the EHG should be approximately 8-10 for a 10-minute window. Skewness, a measure of symmetry, should be small indicating a symmetric EHG waveform. The EHG signal is also expected to have larger frequency components in the 0.1 to 0.5 Hz range.

Accordingly, a quality (or trust) factor (hereinafter referred to as "TF") can be provided using a TF operator of the subject invention, wherein the TF is based on intrinsic properties of the fetal ECG, HR, and/or EHG, and is used to enable the user to quantify signal separation success, automatic recognition of the maternal and fetal channels, and fetal ECG quality (i.e., from 0 (no separation, low quality) to 10). TF operations are performed on the output of Pan Tompkins algorithm operations and on the output of the ICA algorithm, described above, to provide to the user a numerical representation of the quality of the fetal ECG and heart rate values monitored using the system of the invention, which is useful in making diagnostic decisions.

In one embodiment, TF operations include the calculating for each signal at least one continuous probability function with at least one input variable. With the subject invention, these continuous probability functions, called Pf (fetal) and Pm (maternal), represent the probabilities that the output signal in question, found by the ICA algorithm, is respectively a fetal or maternal ECG and its corresponding HR, found by correlation and Pan Tompkins.

Preferably, the probability function is a Gaussian function. This simple mathematical form describes the probability of encountering any given error. As well understood by the skilled artisan, the Gaussian distribution has two free parameters per dimension: the mean and the standard deviation. According to the subject invention, these parameters (i.e., means and variances for each variable) can be fixed or variable. In one embodiment, these parameters can be determined individually or from a sample population.

Preferably, Pf and Pm consists of one or more of the following input variables corresponding to features that are characteristic of fetal or maternal ECG signals, respectively. These variables are compared to ideal values found for clean fetal or maternal ECG signals, or are compared to a combination of past values updated every 4 seconds. Preferably, these input variables include the following:

1. calculation of the estimated fetal heart rate with the autocorrelation function;
2. calculation of the estimated fetal heart rate with the Pan-Tompkins algorithm;
3. variance of the estimated fetal heart rate (from Pan Tompkins algorithm);
4. number of False Positives from Pan Tompkins algorithm;
5. number of False Negatives from Pan Tompkins algorithm;
6. the amplitude of the estimated fetal QRS peaks;
7. the ratio of the autocorrelation peak versus the variance of the autocorrelation function;
8. the sparsity of the estimated fetal ECG signal; and
9. mutual information. Mutual Information is calculated and minimized between the outputs of the ICA algorithm. The minimum value reached for a certain data set represents the quality of the separation and therefore can be used to determined separation quality.

In a preferred embodiment of the ECG trust factor, Pf and Pm have eight (8) input variables corresponding to features that are characteristic of fetal or maternal ECG signals, respectively.

Any one or combination of these input variables can be provided using processes as described below.

a) First, the average HR is calculated from the Pan Tompkins algorithm. For example, the average HR is the median value of the instantaneous HRs found by the Pan Tompkins operations during 4 seconds.

For the calculation of Pf, this average HR is compared to a combination of past values of the average fetal HR, hereinafter called FHRav. FHRav is initialized for all the patients to a value calculated from a sample patient population. By way of example, for a sample patient population of 100 patients, the average FHR was determined to be 145±35 bpm (beats per minute) with a variance of 20±20. This value is then updated every 4 seconds, depending on the previous FHRs found, which are calculated as a function of the trust factor, as described in the following formula:

$$FHRav = \frac{TF}{10} \times FHR + \frac{10 - TF}{10} \times FHRav.$$

When the extracted signal quality is very high, the trust factor is very high and FHRav tends to be equal to the currently found FHR. Likewise, when the trust factor is low, the current FHR is not trustworthy, so a longer term average is used. The HRs found at the end of the Pan Tompkins algorithm are compared to FHRav in the calculation of Pf. The closer the HR is to this value, the more probable the signal is the FECG.

For the calculation of Pm, the HR found is compared to the value of the maternal Heart rate (called MHRav) found by a correlation operation applied on the raw data. The average MHR and its variance can be calculated for each patient because signals corresponding to the maternal channel are easily extracted due to a high maternal influence in sensed signals. For example, unfiltered sensor signals can be passed through an autocorrelation function known to the skilled artisan, wherein overlapping windows of data are correlated to obtain the evolution of the heart rate over a selected period of time. For each autocorrelation signal, the highest peaks corresponding to ECG periodicity are detected and translated to a heart rate, which represents the average MHR, thus allowing for the calculation of the average MHR variance.

Figure 8:
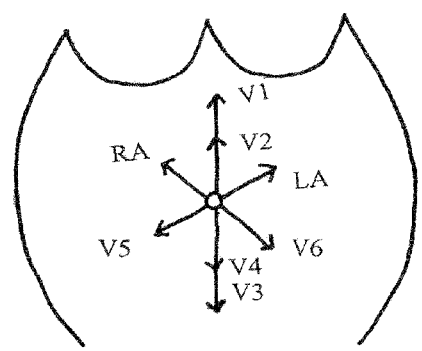
FIG. 8 is an example of a vertex presentation as provided by the subject invention when using sensors positioned on a mesh as provided in FIG. 14.

Preferably, an autocorrelation is performed on the signals closest to the maternal heart (typically RA, LA and v1, see FIG. 8) because these have the strongest maternal influence. A detection algorithm gives the location of the highest peak (beyond the DC offset) and therefore the average maternal RR interval and the average maternal heart rate. The three channels are then combined using a median function to prevent MHR errors caused if one electrode is disconnected or if any kind of problem arises on one or two electrodes.

b) The estimated variance of the HR is compared to a fixed value corresponding to the variance of the FHR/MHR found on a sample population. Preferably, the variance of the HR is compared to 25 in the calculation of Pf and to 4 in the calculation of Pm.

c) Next, the average amplitude of the detected QRS peaks in the output of ICA signal is calculated. The higher the amplitude of the peaks, the more probable the signal is an ECG signal.

d) An estimation of the number of correct beats not detected (false negative—FN); and an estimation of the number of incorrect beats detected (false positive—FP) is also computed from the peaks picked by the Pan Tompkins algorithm. The smaller these numbers are, the more probable the signal is an ECG signal. In a preferred embodiment, acceptable levels of FN and FP are less than 10%.

Also at the end of the ICA algorithm an autocorrelation is performed on the 4-seconds signals. For example, in the preferred embodiment where there are eight input variables, an autocorrelation is performed on eight 4-second signals. For each autocorrelation signal, a peak detection algorithm is performed to determine the highest non-DC peak. For an ECG signal, this peak corresponds to the average RR interval during the 4 second period, and therefore to the average HR (60/RR) during this 4 seconds period. From this autocorrelation method, several parameters are computed for the signals and serve as input to the probability functions:

1. The average HR (which can be determined by using the autocorrelation method described above). If the signal in question is not an ECG signal, this value is not representative of a HR. The closer this HR value is to the previous ECG HR value, the higher the TF will be. The HR is compared to FHRav in the calculation of Pf and to MHRav in the calculation of Pm.
2. The variance of the autocorrelation in between peaks. If the noise level in the signal is low, this value will be low. The lower this value is the higher the trust factor will be.
3. The amplitude of the peak in the autocorrelation function is compared with the variance of the autocorrelation function. The higher this ratio is the higher the TF will be.

Since the ECG signal is characterized by a QRS spike that is significantly larger than the rest of the signal, the sparsity of the ICA output signal is also used as a criterion to determine if it is an ECG signal. The percentage of signal data-points that are less than half of the peak value will be very large in an ECG signal, therefore this parameter is entered into the probability equation.

Another preferred measure of sparsity is Kurtosis. Kurtosis is defined as the normalized fourth central moment of a distribution X:

$$X: \text{kurtosis}(X) = \frac{E[(X-\mu)^4]}{\sigma^4}$$

where $\mu$ is the mean and $\sigma$ the standard deviation of the distribution X. ECG signals typically have a kurtosis much greater than 4 and the noise signals typically have a kurtosis value close to 3 (the kurtosis of the Gaussian distribution). Experimentally, it was verified that for a signal to noise ratio (SNR) greater than 4 dB, FECG and MECG can be clearly identified only by using the kurtosis of the signal.

Mutual Information is calculated and minimized between the outputs of the ICA algorithm. The minimum value reached for a certain data set represents the quality of the separation and therefore can be used to determine separation quality.

In the preferred embodiment, an additional test is performed after the Pan-Tompkins algorithm. In the case where the MHR and the FHR are very close, it is desirable to be able to distinguish the fetal ECG (FECG) and the maternal ECG (MECG) (and therefore the FHR and the MHR). A precise value for the MHR is easy to determine from the raw signal, and therefore the MECG at the output of the ICA algorithm is easy to recognize. From the MECGs, the Pan-Tompkins algorithm gives us the location of the MECG QRS peaks. To detect the fetal channel, the signals that have their QRS peaks at the same location (within a few points range) as the MECG QRS peaks are eliminated. Pf is brought to 0 for these signals.

TF operation in accordance with the subject invention provides the user with a means for assessing the performance and reliability of ICA operations output.

Figure 9:
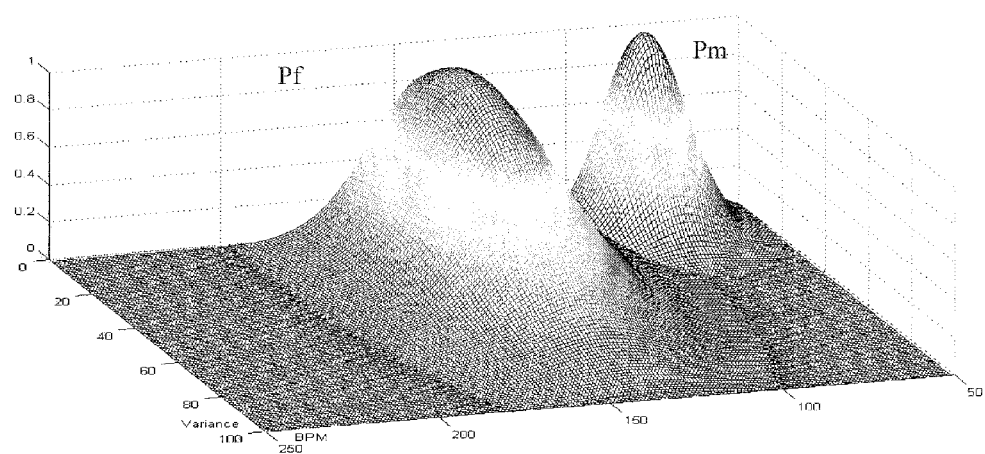
FIG. 9 is a graphical illustration of the probability of a vital signal being from the mother and the fetus, as extracted b a monitoring system of the invention.

In one embodiment, the probability functions for a specific channel (kChan) are defined by the following mathematical and operational relationship: The associated Gaussian distribution curve is provided in FIG. 9.

$$Pm^1 = e^{-0.5\left\{\left(\frac{HR1-MHRav}{10}\right)^2+\left(\frac{HRvar1-4}{10}\right)^2+\left(\frac{AmpPeak-10}{10}\right)^2+\left(\frac{FN+FP}{10}\right)^2\right\}}$$

$$Pf^1 = e^{-0.5\left\{\left(\frac{HR1-FHRav}{20}\right)^2+\left(\frac{HRvar1-25}{20}\right)^2+\left(\frac{AmpPeak-8}{10}\right)^2+\left(\frac{FN+FP}{10}\right)^2\right\}}$$

$$Pm^2 = e^{-\left(\frac{HR2-MHRav}{\sqrt{2}\times 10}\right)^2-\left(\frac{sparsity-750}{\sqrt{2}\times 10}\right)^2}\frac{1}{2}\log(1+0.3r)$$

$$Pf^2 = e^{-\left(\frac{HR2-FHRav}{\sqrt{2}\times 10}\right)^2-\left(\frac{sparsity-700}{\sqrt{2}\times 10}\right)^2}\frac{1}{2}\log(1+0.3r)$$

$$Pm = \text{Max}(Pm^1, Pm^2)$$

$$Pf = \text{Max}(Pf^1, Pf^2)$$

where:
e is the exponential operator;
HR1 is the heart rate calculated for each sensor channel during Pan Tompkins operations;

HR2 is the heart rate calculated for each sensor channel during the autocorrelation operations;

MHRav is the average maternal heart rate;

FHRav is the average fetal heart rate;

HRvar1 is the variance in HR;

FN is the estimated percentage of number of correct beats not detected;

FP is the estimated percentage of number of incorrect beats detected;

AmpPeak is the amplitude of the ECG QRS peaks;

sparsity is the number of points in the signal that are situated below 50% of the maximum (measure of the sparsity of the signal); and r is the ratio between the amplitude of non-DC peak in the autocorrelation function; and the variance of the autocorrelation function.

In another embodiment, the input parameters are used to create membership functions based on the principles of fuzzy logic. Each parameter is compared to the expected value of the parameter and the membership function determines the probability that this parameter is consistent with the appropriate ECG signal. A membership function for the Kurtosis parameter is:

$$e^{-0.5 \cdot \frac{(x-MEAN)^2}{STD\,DEV^2}},$$

where the MEAN is the sample mean for the parameter of interest and the STD DEV is the sample standard deviation of the parameter of interest. An example of the membership function for the Kurtosis parameter is:

$$Pf_1(x) = e^{-0.5 \cdot \frac{(x-8.1)^2}{1.8^2}}$$

$$Pm_1(x) = e^{-0.5 \cdot \frac{(x-22.9)^2}{8^2}}$$

One or more of these membership functions are then combined to create an overall probability for the selection/quality assessment of each channel. This combination can be done in multiple methods, but in this embodiment one of the standard fuzzy logic techniques is used:

$$Pf = \min_i(Pf_i) \text{ and } Pm = \min_i(Pm_i),$$

$$i = 1, 2, 3...$$

According to the subject invention, at the output of the ICA algorithm and Pan Tompkins algorithm operations, TF operations are performed on estimated signal results. TF operations include computing the probabilities for Pf and Pm, see FIG. 9; and comparing the two probability values to classify whether the signal result is a maternal signal (i.e., maternal ECG), a fetal signal (i.e., fetal ECG), or other signal such as noise.

In certain embodiments, a TF is computed by truncating the value of 10 times the highest probability Pf. It ranges from 0 to 10 (where 10 corresponds to a probability of 1). 0 is the worst case where the signal is very unlikely to be a fetal ECG and is most-likely noise. 10 is the best case where the fetal ECG is well detected and the value of the heart rate that is calculated using Pan Tompkins operations is an accurate value.

4—Maternal-Fetal Channel Determination Operations

The output signals of ICA operators are generally of arbitrary scale and order. In addition, as the signal changes, the location of the fetal signal channel is likely to change as well (i.e., during contractions, the contraction signals become larger and produce different overall signal characteristics, both raw and separated). Thus, detecting which channels are maternal ECG, fetal ECG, and noise is beneficial to the user. Currently, channel classification is a complex task normally performed manually by skilled clinicians. The subject invention advantageously provides automatic, real-time classification of maternal and fetal output channels to enable appropriate processing algorithm operations, such as those described above, on desired signals.

Maternal-fetal channel determination operations are performed on the TF operator(s) output. TF operator(s) output is processed by maternal-fetal channel determination operator(s) to identify the highest Pm and Pf values, which corresponds to the probability of the signal being a maternal or fetal signal channel, respectively. In a preferred embodiment, a signal is classified as a maternal signal when Pm>Pf and Pm>0.7. On the remaining signals (not classified as maternal signal), the signal with the highest Pf is classified as a fetal channel.

For cases where the FHR and the MHR are very close, the location of the QRS peaks is an important source of information to differentiate the two signals, since it is very unlikely that the fetal and maternal waveforms will be synchronized totally. The locations of the maternal QRS peaks are found in the electrodes closest to the maternal heart and with the Pan-Tompkins method, since the maternal ECG is very strong in these channels. At the output of the Pan-Tompkins algorithm, all the signals that have QRS peaks at the same location as the MECG (with 20 ms precision allowed) are eliminated by bringing their membership functions to zero.

5—EHG Extraction Operations

According to the subject invention, EHG extraction operations comprise (1) down-sample operator(s); (2) filtering operator(s); and (3) contraction detection operator(s). Any signals from sensors of the invention can be used in EHG extraction operations. In a preferred embodiment, signals from sensors located along the vertical midline of the maternal abdomen are input to EHG extraction operator(s).

Figure 10:
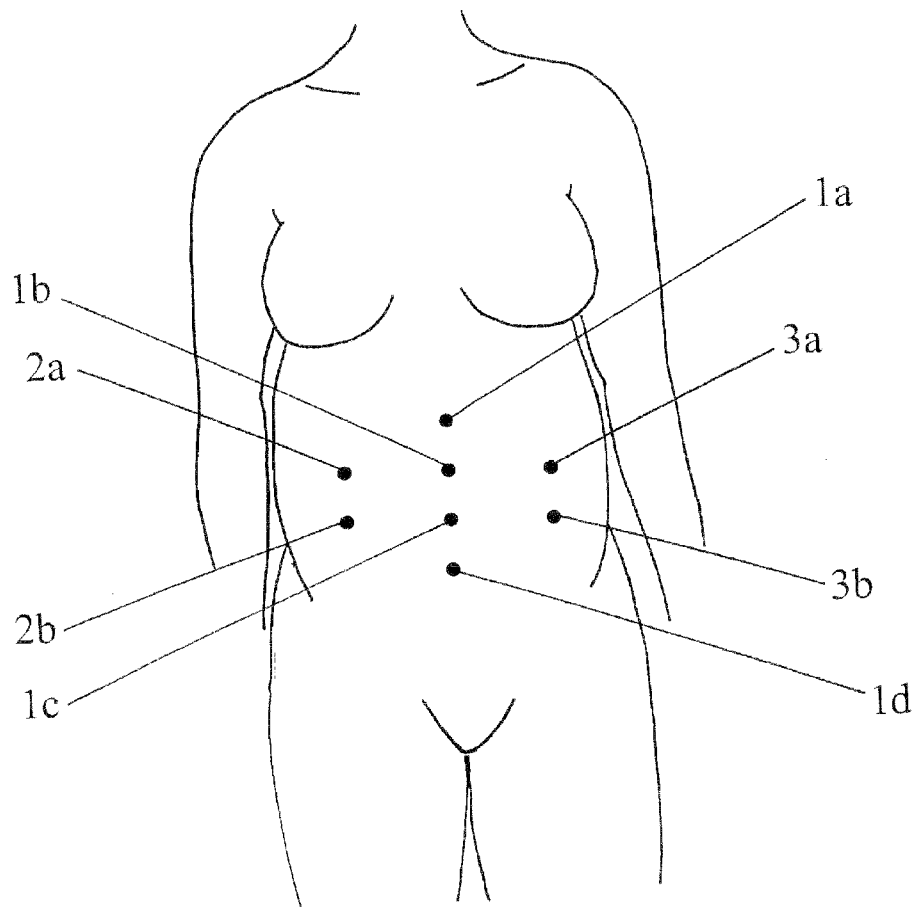
FIG. 10 illustrates a set of electrodes positioned on a maternal abdomen in accordance with the subject invention.
Figure 11A:
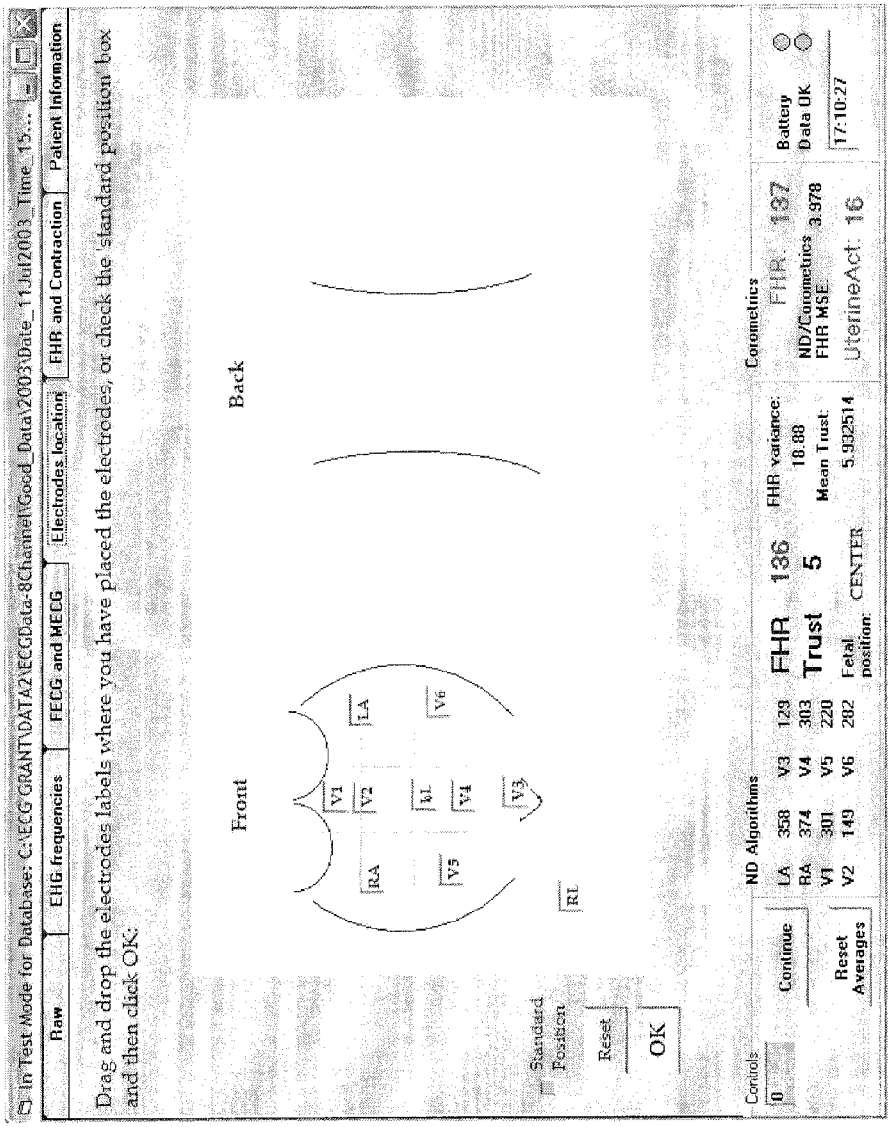
Figure 11B:
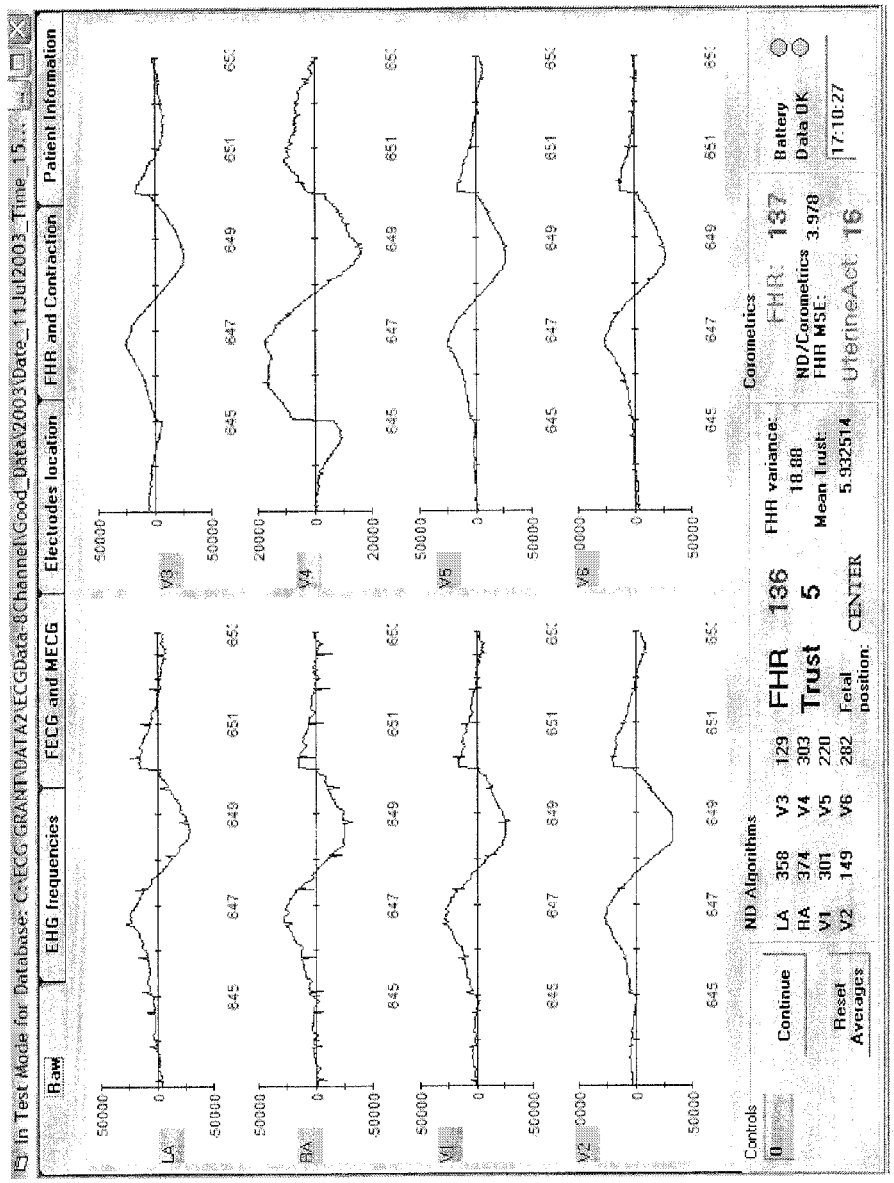
Figure 11C:
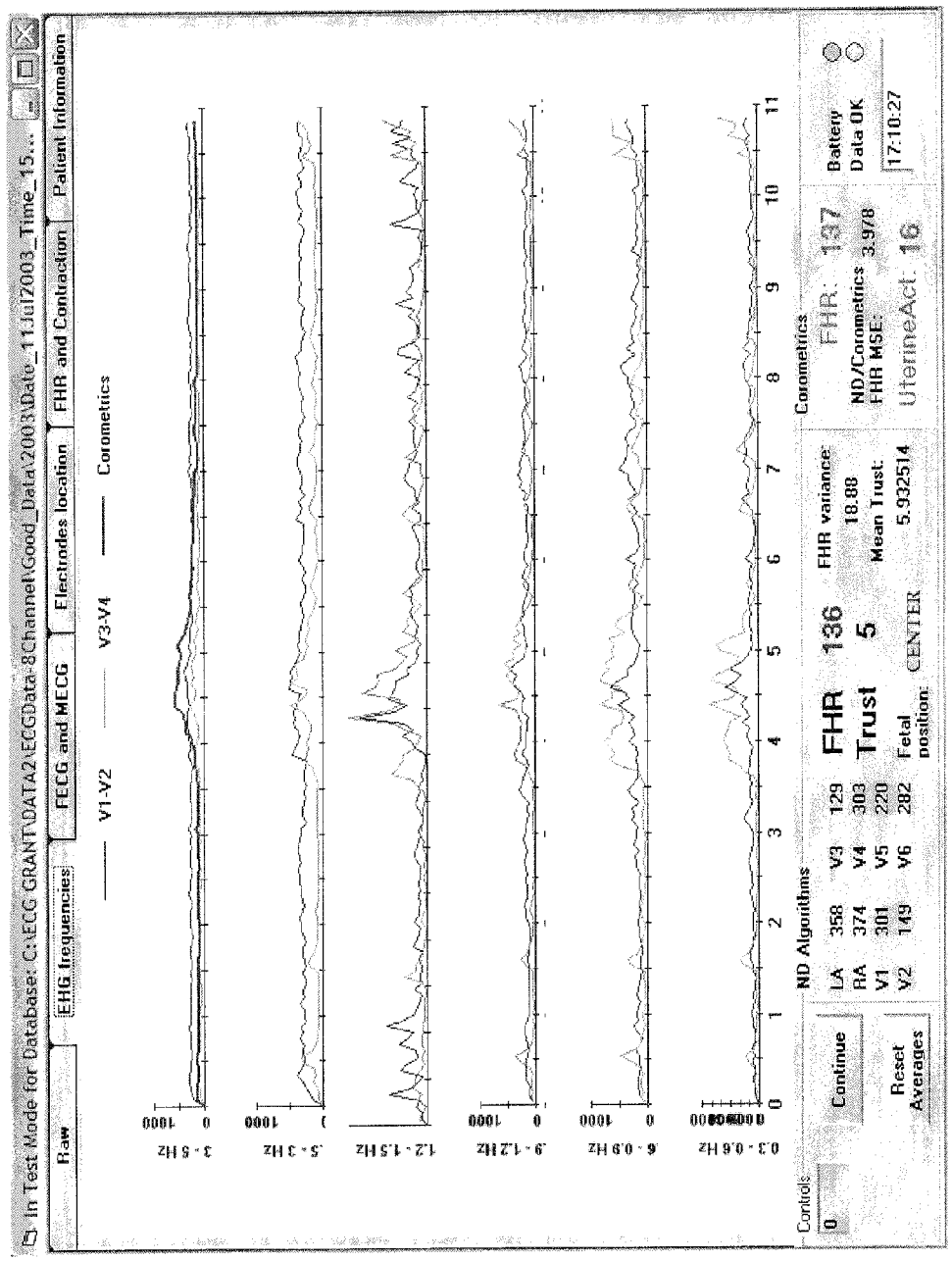
Figure 11D:
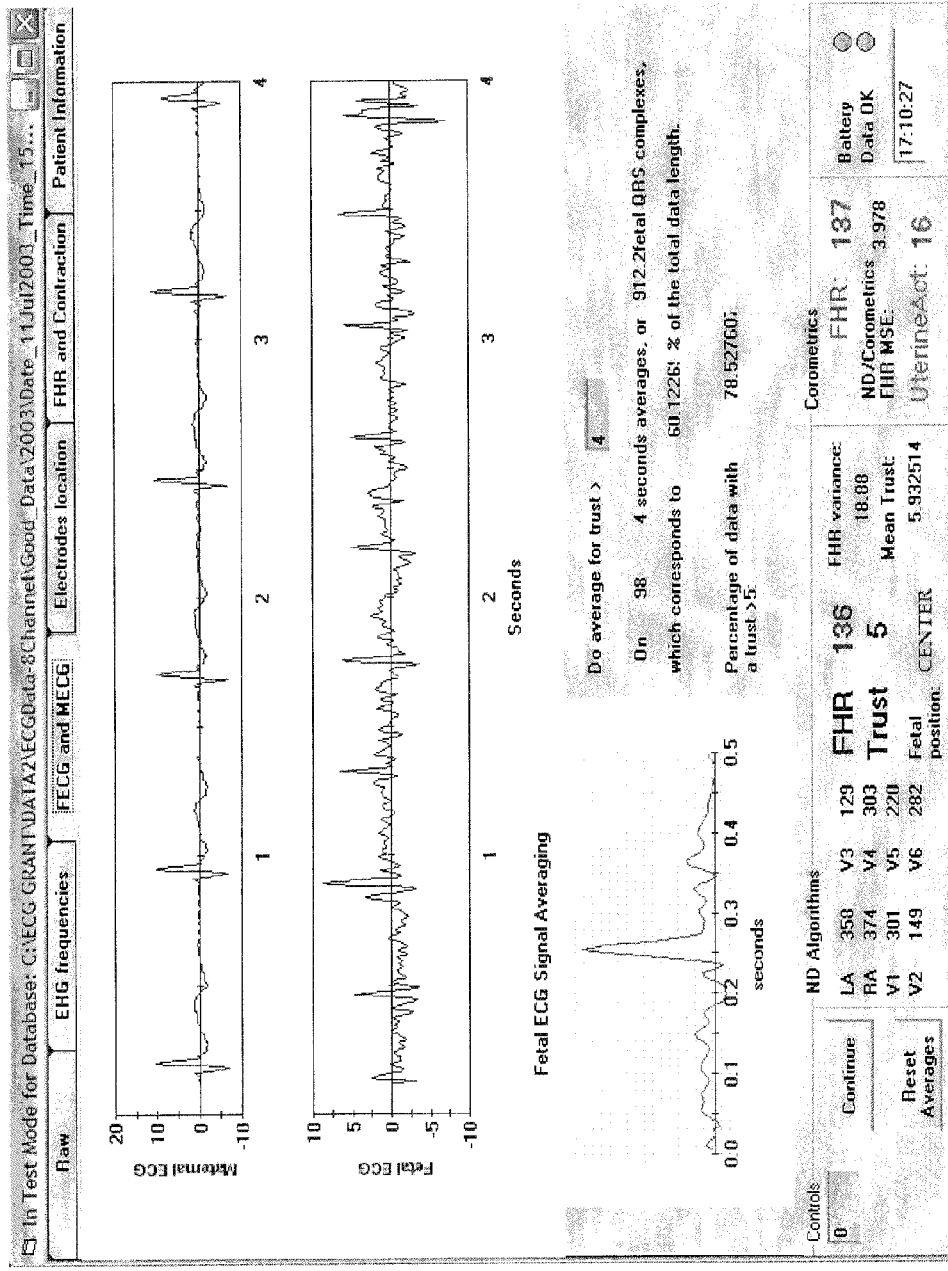
Figure 11E:
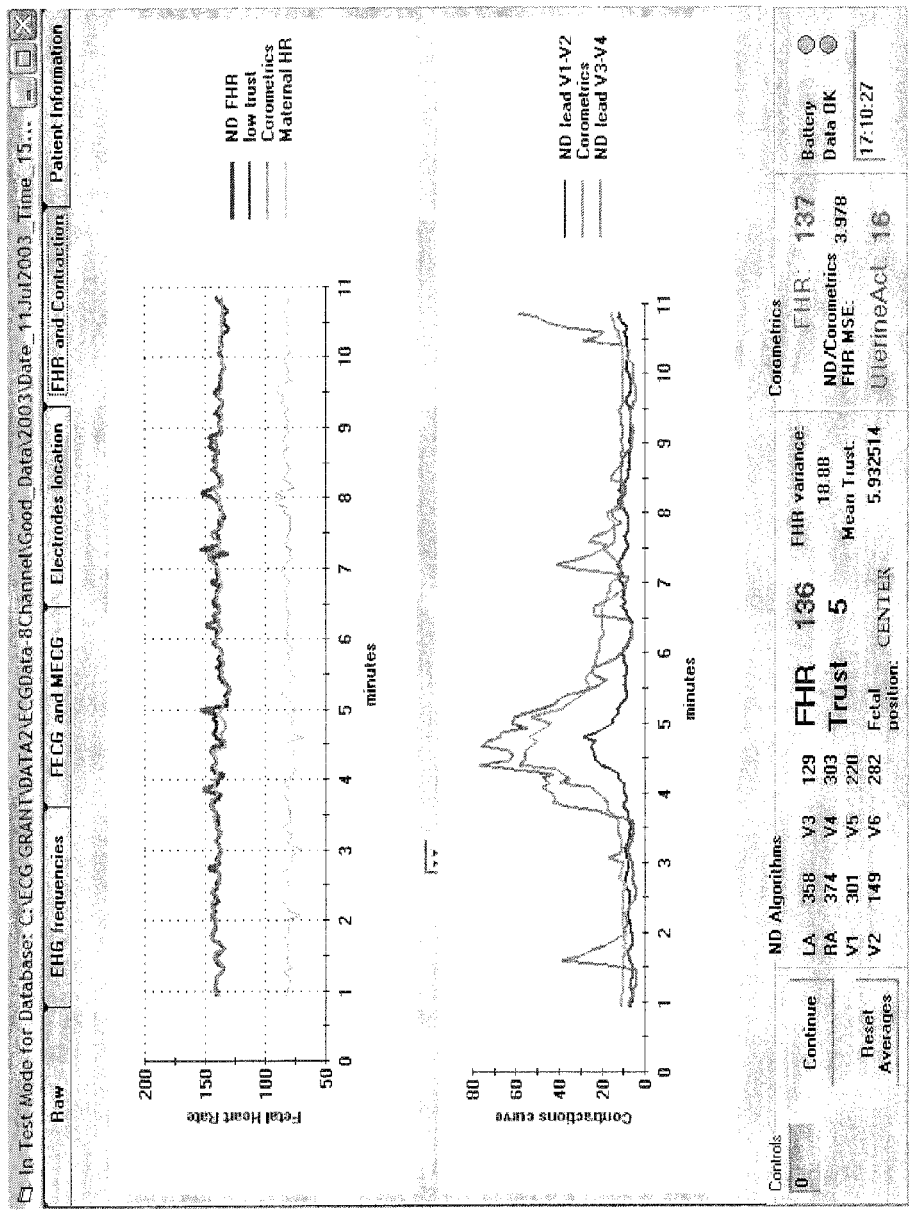

Because EHG signal frequencies are often in a low frequency range (<5 Hz), input signals received from an amplifier (and A/D converter) are communicated to down sample operator(s) to remove extraneous high-frequency information. For example, where signals from eight channels (see FIG. 10, sensors 1*a*-1*d*) are sampled originally at a frequency of 200 Hz, the down sample operator(s) reduces the sample rate to 20 Hz. The down-sampling of the EHG is desired so as to reduce the volume of data to be processed by the computing means. In addition, at the output of the down-sample operator(s), a non linear operator can be performed on a combination of the down sampled signals. Preferably the nonlinear operator is the absolute value operator and the combination of channels is a pair wise difference:

$$1_{ab} = |1_a - 1_b|; \text{ and } 1_{cd} = |1_c - 1_d|.$$

These operator(s) output (absolute values of $1_{ab}$ and $1_{cd}$) are communicated to filtering operator(s) to obtain the envelope of an EHG wave. Known digital filters can be used to perform EHG extraction/filtering operations. In one embodiment, a low pass Butterworth filter (i.e., of order 4, having a cut off frequency 0.05 Hz) is used to obtain the envelope or slow wave of at least one EHG wave.

Output from filtering operator(s) is input into contraction detection operator(s) to detect the beginning, end, duration and amplitude of a uterine muscle contraction. The contraction detection algorithm operation relies on identifying those segments in the EHG results that have values exceeding a particular threshold level for a specified duration. In order to determine the threshold, the contraction detection operator(s) analyze filtering operator(s) output signals using a specified time frame (or window). In one embodiment, filtering operator(s) output signals are analyzed by contraction detection operator(s) in 4 minute wide windows, with 1 minute shifts.

According to the subject invention, with every contraction detection operation, the signal samples (filtering operator(s) output) in a window are processed to obtain a basal tone and a threshold for normal versus contraction activity. To determine the threshold for detection of contraction changes, contraction detection operator(s) add 25% of the windowed signal range to the basal tone. Thus, the threshold for detection of contractions can change according to the signal level. In accordance with the subject invention, a contraction can be recognized if the duration of an EMG result is greater than a set period of time (i.e., 30 seconds) and the amplitude is greater than a percentage over the threshold value.

Contraction determination operations of the invention also include determining the intensity of contraction, which represents the number of spikes during every uterine contraction. Contraction intensity determination, as performed by contraction-determination operator(s) of the invention, requires estimation of the timing parameters (starting time and duration) of the contraction signal. In accordance with the subject invention, to determine contraction intensity, filtering operation output (high frequency signal, $1_{ab}$ and $1_{cd}$) is input to another filter operator(s) to smooth (i.e., remove high frequencies) the paired sensor signals. In one embodiment, the sensor signals are smoothed by a low pass Butterworth filter ($4^{th}$ order) with cut off frequency 0.4 Hz. After "smoothing", the contraction determination operator(s) determine the number of positive peaks in each contraction. Only those contraction signal peaks having width greater than 2 seconds and amplitude greater than 25% of the contraction amplitude are analyzed.

Further, according to the subject invention, EHG extraction operation includes providing an EHG spectrogram and contraction curve. In one embodiment, the EHG spectrogram and contraction curve are plotted on a graphical user interface of the invention. In a preferred embodiment, the contraction curve is plotted below the fetal heart rate and maternal heart rate trace. It has been conjectured in the literature that contraction efficiency may be determined with appropriate analysis of the frequency content of the EHG signal. Moreover, spectral characteristics of the EHG curve may be able to be used to predict contraction efficiency and preterm labor. Accordingly, the present invention can convert EHG signals into values proportional to the pressure in the uterus (i.e., IUPC) or directly to montevideo units, which to date has not been contemplated for monitoring systems. In further embodiments, the present invention utilizes neural network systems to convert EHG signals into Montevideo units. The frequency content of the EHG, as typically shown in a spectrogram such as those illustrated in FIGS. 11B-11E, and other results provided by EHG extraction operations can aid the user in estimating or be used to determine contraction effectiveness, detecting false versus real labor (i.e., useful in saving trips to the hospital for Braxton Hicks contractions), probability of vaginal delivery (or conversely, the need for a C-section), time to delivery, arrested descent, uterine rupture, and labor progress. As described above, this system could be used as a home monitoring system that not only continuously monitors fetal heart rate and ECG to detect fetal well-being, but also can be used to determine the difference between effective and non-effective contractions and false versus real labor.

In addition, the electrical signal from the abdomen (the EHG coupled with the EMG of abdominal muscles) could be used as a biofeedback mechanism to help direct maternal pushing effort during the second stage of labor. Such feedback may be particularly helpful when neuraxial analgesia has blunted sensation from the abdomen and perineum.

6—ECG Waveform Reconstruction Operations

It is well understood by the skilled clinician that heart defects can be detected by analyzing the different intervals and segments of ECGs. To determine normal ECG values for the fetal heart, which is applicable to fetal health (and heart health) during pregnancy or labor, more than the location of the heartbeat (the QRS segment) might be required. For example, the lower frequency attributes of the ECG signal, such as the P and T waves, can be useful in determining fetal heart standards, the early diagnosis of fetal heart defects, as well as establishing fetal health.

At the output of ICA algorithm operations, different signals may have been distorted by different filtering operations (i.e., including preprocessing filtering with the amplifier). For example, ICA operations output often include fetal ECGs having P and T wave amplitudes comparable to the noise amplitude. This makes these waves difficult to detect. State of the art monitoring systems are unable to provide accurate fetal ECG waveforms (including lower frequency P and T waves) as well as to eliminate the high frequency noise and the base line wander. Normally, P and T wave frequencies are in the 1 to 5 Hz range for the maternal ECG and from 2 to 10 Hz for the fetal ECG. The base line wander is in the 0 to 3 Hz range and the high frequency noise, mainly due to the power line interference is approximately 60 Hz.

Generally, the QRS peaks of ECG results are generally visible post ICA operations. However the fetal ECG signal output of ICA operations is commonly unrecognizable as an ECG signal by skilled physicians, who are accustomed to observing clean adult ECGs.

In accordance with the subject invention, in certain embodiments of the monitoring system it is desirable to reconstruct a "reshaped" fetal ECG source. In one embodiment of the invention, at least one known filter is used to perform ECG waveform reconstruction operations on ICA operations output. In a related embodiment, an inverse filter and then a band pass filter are used by ECG waveform reconstruction operator(s) to reconstruct and highlight the different waves present in ECGs signal/ICA operations output (in particular fetal ECG signals) while removing high frequency noise and base line wander.

In a preferred embodiment, the following inverse filter operator (used in ECG waveform reconstruction operations) is defined by the inverse of the preprocessing filter: $H(z)=1/(1-0.99z^{-2})$.

The band pass filters used in ECG waveform reconstruction operations are FIR filters. In a preferred embodiment, for the maternal ECG signal, an FIR filter of order 40 and of band [2 Hz, 50 Hz] is used. For the fetal ECG signal, an FIR filter of order 30 and of band [5 Hz, 50 Hz] is used. According to the subject invention, the fetal ECG (and maternal ECG) waveforms can be plotted on a graded figure so as to enable the user to extract the different ECG intervals and segments that are useful in diagnosis/determining clinical strategy. Similarly, the ECG intervals can be calculated automatically by the processing means.

As described above, further embodiments of the invention provide a computing means that includes a storage means. The storage means can collect and/or display via the graphical user interface, ECG waveform reconstruction operations output (i.e., ECG reconstructed waveforms having both P and T waves) as well as ICA operations output (i.e., ECG with highlighted QRS spikes and P and T wave removal with other noises).

In certain embodiments, the invention provides a software means for analyzing reconstructed ECGs, in particular, the fetal ECG. The reconstructed fetal ECG can be used to diagnose fetal acidosis and cardiac arrhythmias.

7—Operations for Determining Fetal Heart Electrical Influence in Different Sensors During the first two trimesters of gestation, the fetoabdominal volume conductor can be considered as a homogenous volume conductor and therefore the closer the electrode is to the fetal heart the higher the amplitude of the fetal ECG signal from the sensor(s). According to the subject invention, the location of the sensors (i.e., electrodes) corresponding to the highest coefficients provides the user with the location of the fetus in the uterus (low, high, right, left). The electrodes corresponding to the lowest coefficients can be moved to the region where the fetus is located in the abdomen to obtain raw signals with higher fetal influence (thus improving system performance).

From the $27^{th}$ to the $37^{th}$ weeks of gestation, a highly resistive layer surrounds the fetus: the vernix caseosa. Measurements confirm the model with a high resistivity layer (vernix) with 2 holes that are situated on the vertical axis. The two most probable pathways are the oronasal cavities situated over the head of the fetus and the umbiliculus situated at the other end of the fetal torso. During this period the current flows are not transmitted homogeneously within the abdomen and the influence of the fetal ECG in the different sensor channels may not correspond to the fetal position in the uterus. However the user can still move the sensors, which have been determined to have low fetal influence using operations described below, to better locations on the maternal abdomen.

In accordance with the subject invention, the ICA algorithm operations performance (i.e., as quantified by TF output) depends on the quality of the raw signals and the relative amplitude of the fetal ECG in the raw data (prior to filtering operations). Accordingly, ICA algorithm operations output is a function of sensor position. The following operations for determining fetal heart electrical influence in sensors include the function of optimizing ICA algorithm operator(s) output.

Figure 12:
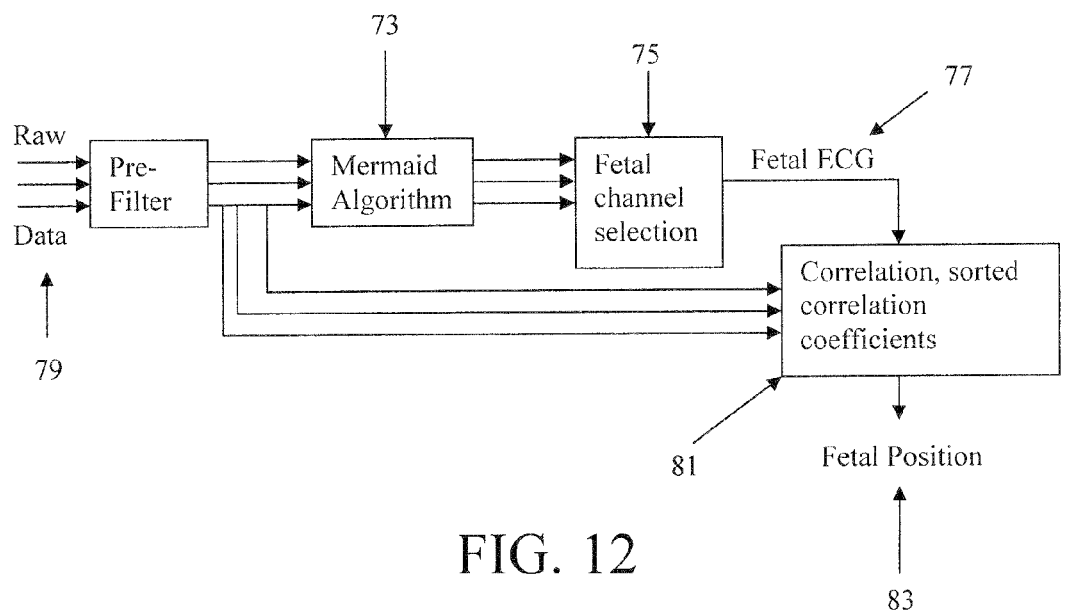
FIG. 12 is a flow diagram illustrating steps for determining the fetal heart electrical influence on different sensors in accordance with the system of the invention.

Operations for determining fetal heart electrical influence in sensors of the invention include input-output matching for correlating ICA operator(s) output with raw sensor input (i.e., non-filtered sensor input), see FIG. 12. For example, at the output of ICA algorithm 73 and maternal-fetal channel determination 75 operations, the estimated fetal ECG signal 77 (or a projection of this fetal ECG signal based on the orientation of the electrodes and fetus) can be correlated 81 with the original, raw sensor signal channels 79. The resultant correlation coefficients correspond to the influence of the fetal heart electrical influence in the different electrodes, and are provided to the user. Further, the correlation coefficients can be used in presenting to the user fetal position 83.

Assuming the relationships between signals are linear, correlation techniques determine if a sensor signal output "resembles" another signal output, since these methods detect linear dependencies between signals. However, the linear dependency assumption is simplistic in the case of real data. Mutual information (MI) is a measure of dependencies (linear or non-linear) between signals. MI is null when the signals are independent. Thus, as the MI value increases, the strength of the dependency between the signals increases accordingly. With such cases, instead of simple correlation between the output of the ICA and the raw data, the input-output matching means can include calculating the mutual information value between the signals to find out the influence of the fetal signal output in each raw signal.

Alternatively, input-output matching means can be provided using non-linear matching methodologies. Neural network systems are non-linear adaptive systems that can detect non-linear dependencies between signals. Using a filtered version of the output of the ICA algorithm as a template and neural network, the influence of the fetal electrical activity in the different channels can be determined.

In certain situations, the ICA algorithm operator(s) output may not be optimal and/or the estimated fetal ECG may not be extracted. Although correlation of the estimated ECG signals and the raw signals can still be calculated, since the fetal channel may not contain any actual fetal ECG signal, the correlation coefficients may be skewed. To address this possibility, the subject invention correlation is performed based on TF operations output. For example, since the trust factor operations output quantifies the performance of ICA algorithm operations, when TF operations output is lower than a set value, correlation calculation is not performed and the user is notified. In a preferred embodiment, a user is notified that correlation calculations will not be performed when TF operations output is lower than 2. The user can then change the position of the electrodes to obtain better signals (or correlation coefficients).

In one embodiment, the position of the electrodes is provided to the user on a graphical user interface. In the graphical user interface, a page is created to allow the user to display the placement of the electrodes on the maternal abdomen (i.e., on a drawing). Where a set of electrode on a mesh is used, the position of the electrodes is always known and recognized by the computing means.

Using the correlation coefficients provided by operations for determining fetal electrical heart influence in the sensors enables the user of the invention to fine tune the sensor placement for better signal positioning.

8—Fetal Presentation Operations

Fetal presentation impacts labor and delivery with the potential for prolongation of labor, increased pain and/or labor dystocia (inability to deliver vaginally) and possibly fetal distress and complications. While fetal presentation is normally determined by palpation of fetal parts through the maternal abdomen, accuracy depends on the skill of the examiner, as well as the girth of the patient. During labor the cervical examination can help identify the orientation of the fetal head (or presence of a different presenting part, e.g., foot or buttocks), but again depends on the skill of the examiner and the quality of the examination (dilation of the cervix, etc.). When doubt remains, ultrasound can usually identify the fetal presentation, if not the orientation of the presenting part (e.g., occiput direction). However, a routinely applied monitor that alerts the clinician to an abnormal presentation early on may reduce complications. For example, if a breech position is detected, either an external cephalic version (flipping the baby over) attempted, or elective cesarean delivery.

As known by the skilled artisan, different signals from different sensors placed on the maternal abdomen represent different projections of the fetal heart vector. As understood by the skilled clinician, different waveforms of fetal ECG signals have different shapes depending on the location/orientation of signal collection. In one embodiment of the invention, models of the fetal heart vector for different fetal presentations are created and the models are projected onto the 8 different signals (often called leads) to assess the quality of sensor placement. Templates of simulated fetal ECG waveforms corresponding to different fetal presentation in the uterus are then presented to an input-output matching means. In one embodiment, each template is correlated (or "matched") with the raw data at the location of the fetal QRS complex. Accurate fetal presentation is provided by the highest correlation coefficient.

As known to the skilled clinician, the heart possesses an underlying activation structure that serves the mechanical function of the heart as pump. The anatomy of the fetal heart differs from the adult heart in its mechanical functioning. As oxygen is supplied to the fetus by the placenta, the need for pumping blood through the lungs is not there. Postnatally, the left ventricle of the heart is pumping blood to the body and the right ventricle blood to the lungs. In the fetus both ventricles pump blood primarily to the body.

Figure 13:
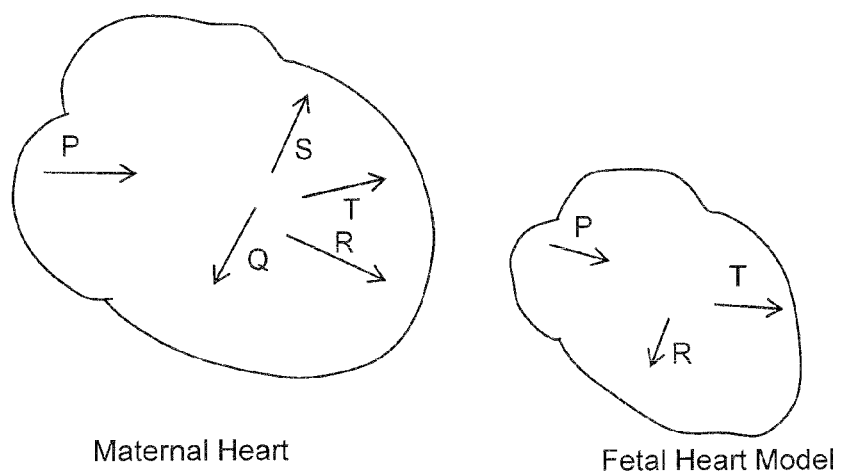
FIG. 13 illustrates models for fetal heart vectors and maternal heart vectors in accordance with the subject invention.

As illustrated in FIG. 13, the maximum amplitude of the QRS complex for fetus and young children 90 is found when it points to the right-anterior inferior octant, whereas for adults it is rotated over 90 degrees and points to the left. For the P wave, in general, the same direction is observed in the fetal heart as in the adult heart 92, pointing from the right to the left atrium. Data (as collected from newborns) show that it is likely that both P and T waves point in more or less the same direction and the R peak is more or less under an angle of 90 degrees with these other two. In this configuration, it is primarily the QRS complex that shows a different direction in the fetal case 90 when compared to the adult case 92.

In one embodiment of the invention, it is assumed that the dipole model of the postnatal case resembles the prenatal case. The amplitude of the dipole representing both P and T wave is about one sixth of that of the QRS complex.

Depending on the fetal presentation as determined using operations described below, the fetal heart vector model has to be rotated. Then fetal presentation operator(s) project the different wave vectors onto the basis made by the different sensors (such as 8 electrodes of FIGS. 10 and 14) and a simulated fetal QRS complex for each electrode is obtained.

Figure 14:
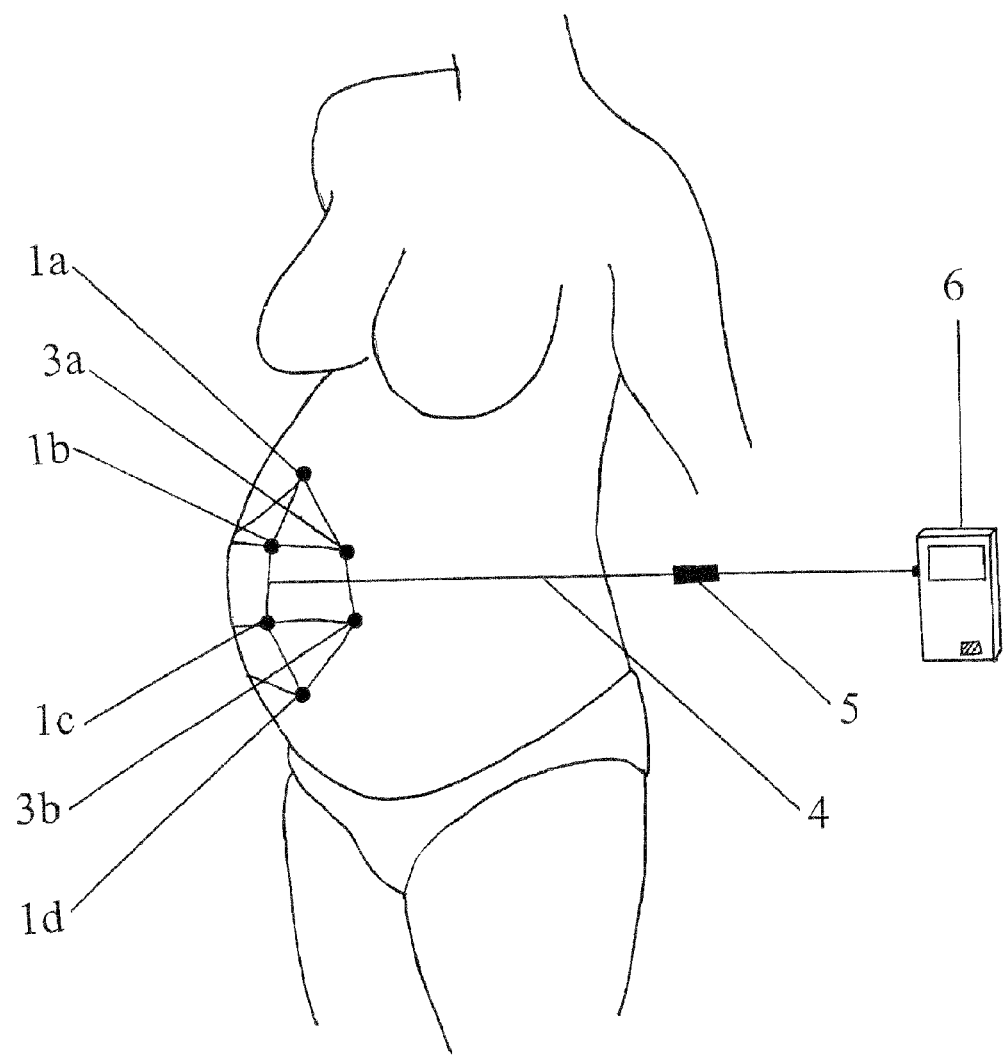
FIG. 14 illustrates an ambulatory maternal-fetal monitoring system for use in accordance with the subject invention.
Figure 15:
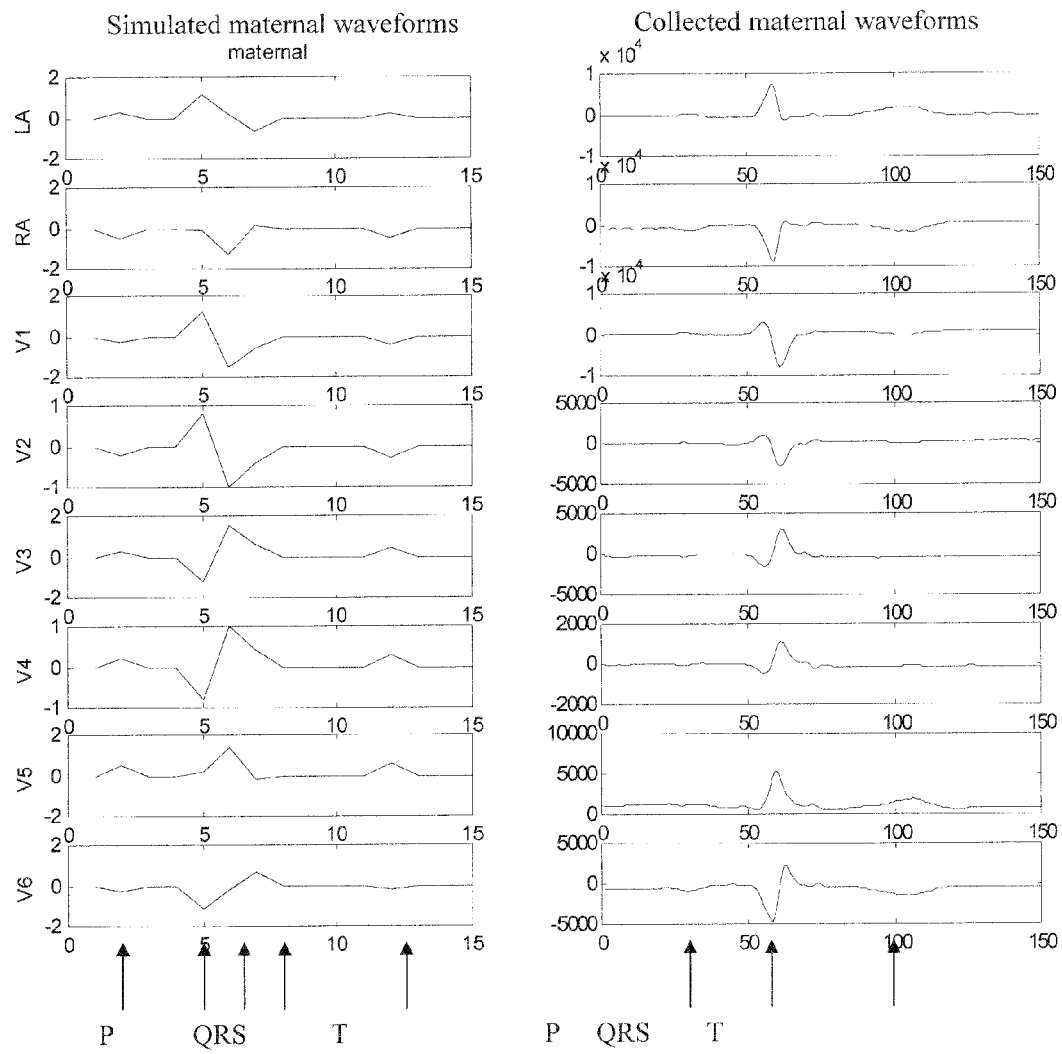
FIG. 15 is an illustration comparing simulated ECG waveform versus collected ECG waveform for each electrode ($V_{1-6}$, RA, and LA).

The electrodes ($V_1$, $V_2$, $V_3$, $V_4$, $V_5$, $V_6$, RA, and LA) are positioned on a maternal abdomen in FIG. 8A using a mesh as seen in FIG. 14. With a sensor-mesh, for pregnant women without heart problems or diseases, the shape of ECG waveforms should be similar to a template of simulated maternal waveforms, as long as the sensor positions remain unchanged. An example of a model for vertex presentation using the electrodes of FIG. 8A is provided in FIG. 8B. FIG. 15 shows maternal simulated ECG waveforms for each electrode 100 in comparison against the actual, collected waveforms for each electrode 102.

Figure 16:
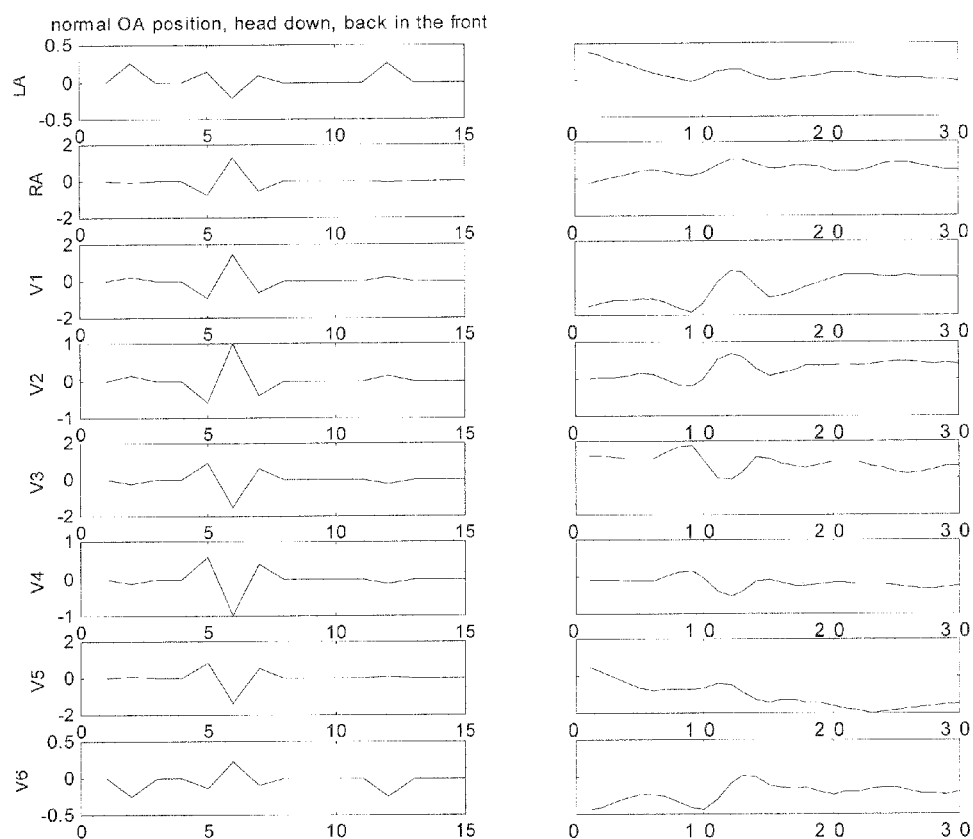
FIG. 16 illustrates a simulated fetal ECG waveform for a specific fetal position as compared to collected ECG waveform for each electrode ($V_{1-6}$, RA, and LA).

As described above, fetal ECG waveforms depend on the fetal presentation. FIG. 16 shows the simulated fetal ECG waveforms 104 that should be obtained with the sensors placed in positions as described in FIG. 8 when the fetus is in a normal OA position, head down, back in front. As illustrated in FIG. 16, the collected ECG waveforms 106 substantially correspond to the simulated ECG waveforms 104, wherein most of the differences can be attributed to a mixture of noise and maternal ECG.

Figure 17A:
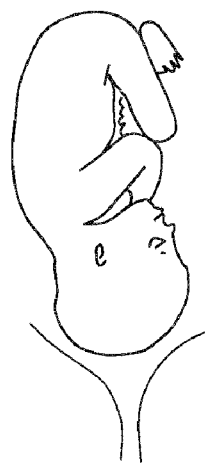
FIG. 17A-C illustrate various templates corresponding to different fetal presentations in the maternal abdomen that are provided in accordance with the present invention.
Figure 17B:
Figure 17C:
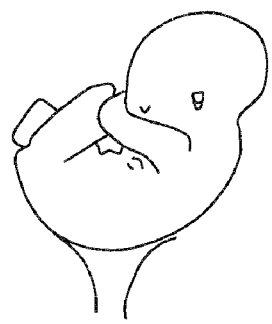

In accordance with the subject invention, a variety of templates corresponding to different fetal presentations can be provided and correlated with the collected waveforms and the template that provides the highest correlation coefficient corresponds to the estimated fetal presentation. The following are different templates of the invention, without limitation:

Vertex (96.8% of pregnancies) as illustrated in FIG. 17A; Breech (2.5% of pregnancies) as illustrated in FIG. 17B; and Shoulder (0.4% of pregnancies) as illustrated in FIG. 17C.

9—Intra-Uterine Pressure (IUP) Operations

Mechanical contractions are the manifestation of the cyclic polarization and depolarization of the uterine muscles. The spontaneous electrical discharge in the muscle from the uterus consists of intermittent bursts of spike discharges (action potentials), characterized by slow and fast waves. The slow wave is associated with the appearance of bursts while the fast wave determines the rate of firing of individual spikes within the bursts, and hence represents the contraction intensity. This electrical activity of the uterus increases the intrauterine pressure, thereby exerting force on the abdominal wall inducing mechanical contractions.

In certain embodiments, non-invasive and real-time estimation of intra-uterine pressure (IUP) can be determined using a means for estimating intra-uterine pressure. In certain embodiments, the means for estimating IUP includes software analysis of EHG extraction operations output. In other embodiments, a neural network (or other intelligence methods) system is provided to analyze EHG extraction operations output to determine IUP. According to the subject invention, a multi layer perceptron (MLP) can be used to estimate the IUP signal from the EHG, wherein the frequency information in the EHG from EHG extraction operations output is used. In a preferred embodiment, the MLP can be trained with an error that is weighted more heavily during contractions. In an additional embodiment, a signal derived from the EHG can be extracted that is not identical to the IUP signal, but yet contains clinically relevant information that can be used in lieu of the IUP signal.

In accordance with the subject invention, an extracted signal derived from the EHG that contains clinically relevant information that can be used in lieu of the IUP signal (also referred to herein as the "IUP-like signal") can be used for a variety of purposes. For example, the IUP-like signal can be used to evaluate labor progression including evaluating contraction efficiency, the effectiveness of drugs used to induce labor, likelihood of labor dystocia, and/or to provide feedback as to the effectiveness of maternal expulsive efforts.

In a related embodiment, EHG extraction operations or IUP-like signals can be used during the post-partum period.

In one embodiment, the spectrogram of the EHG data set is computed over a window of 2000 samples and is divided into 18 different bands of frequencies ranging from 0-100 Hz. The average energy in every frequency bin (i.e., 18 frequency bins) for the 8 channels is given as input to a neural network system (144 inputs). The window is shifted by 100 samples and the spectrogram computation is repeated. Thus the input to the MLP is the evolution of frequencies in the EHG over time.

Figure 18:
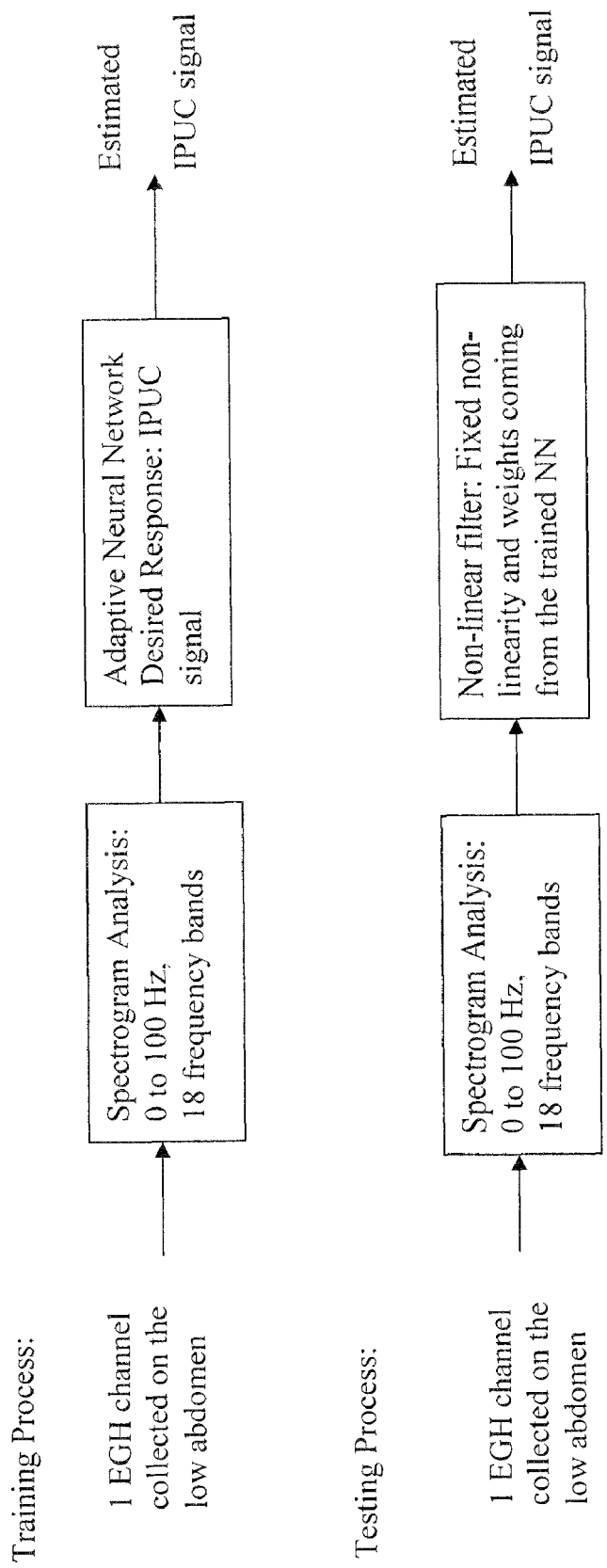
FIG. 18 illustrates the steps of training and testing processes for an intra-uterine pressure sensor of the invention.

In a preferred embodiment, the MLP has 18 input processing elements (PEs), 5 hidden layer PEs, and an output PE. Both the hidden and output layers have hyperbolic tangent non-linearities. As understood by skilled engineers in the field, the training stage on a neural network system is performed on a large number of data sets using an IUP catheter (IUPC), see FIG. 18. The data is passed through the network repeatedly, and each time an error between the desired output of the network and the actual output of the network is computed. This error is used to adjust the parameters of the network to reduce the error. After repeated training passes, the error is minimized and the neural network is ready for use (typically, at this point, the system parameters are fixed). In the testing process, a set of data that was not used for training is passed through the system to ensure that the neural network has appropriately learned the task.

As understood by the skilled clinician, IUP is not homogenous in the uterus. Current usage of IUP catheters provides imprecise IUP measurement because IUP catheter output depends on the position of the catheter, the volume of amniotic fluid, and the position of the patient. Because the sensors of the subject invention can be placed at various locations on the abdomen, the pressure calculated by different sensors gives a different value for each sensor. In a preferred embodiment, a sensor is placed low on the abdomen, near the lower part of the uterus.

Following are examples that illustrate procedures for practicing the invention. These examples should not be construed as limiting. All percentages are by weight and all solvent mixture proportions are by volume unless otherwise noted.

EXAMPLE 1

Monitoring of EHG Data

EHG data was collected from over 500 patients using an EHG monitoring system such as those disclosed in U.S. patent application Ser. No. 10/857,107.

Following skin preparation by gentle rubbing with an abrasive gel, an array of eight 3-cm$^2$ Ag/AgCl$_2$ electrodes (Ambu; Glen Burnie, MD) was placed over the maternal abdomen (FIG. 1) and signals amplified with high gain (60 dB+) low noise amplifiers. All eight signals were measured with respect to a reference electrode.

One amplifier was provided that used a driven right leg (DRL) circuitry to reduce common mode noise between the patient and the amplifier common. The amplifier 3 dB bandwidth was 0.1 Hz and 100 Hz, with a 60 Hz notch.

Data extracted from the electrodes were transferred to a personal computer (PC) via a 16-bit resolution A/D card and stored at a 200 Hz sampling frequency. In addition to electrical signals, data from a standard maternal-fetal monitor (Corometrics, GE Medical Systems) were also collected for comparison purposes.

EXAMPLE 2

Comparison of Contraction Data

Figure 2:
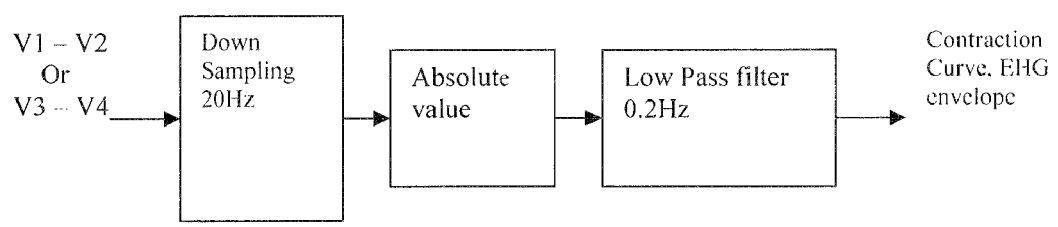
FIG. 2 is a flow diagram illustrating the steps involved in establishing contraction activity based on EHG data collected via the array of electrodes illustrated in FIG. 1.

A study was performed to assess the accuracy of contraction data calculated from extracted EHG data when compared against data extracted via an IUPC. EHG data was extracted using the maternal-fetal monitoring system described in Example 1. In order to visualize and quantify the electrohysterogram (EHG), the signals from the electrodes were preprocessed (FIG. 2) to establish the envelope of the EHG signal ("envelope," in signal processing terms is similar to the average energy) that can be directly compared with contraction data extracted using an IUPC (intrauterine pressure catheter). In an alternative embodiment, the EHG signals could be preprocessed for direct comparison with a tocodynamometer.

In this study, EHG data from the study described in Example 1 was compared against IUPC data collected from a study of 64 different patients and a gestational age greater than or equal to 35. Using the maternal-fetal monitoring system of Example 1, up to 94.7% of approximately 3900 contractions were accurately detected with a standard deviation of 8.6%.

Figure 3:
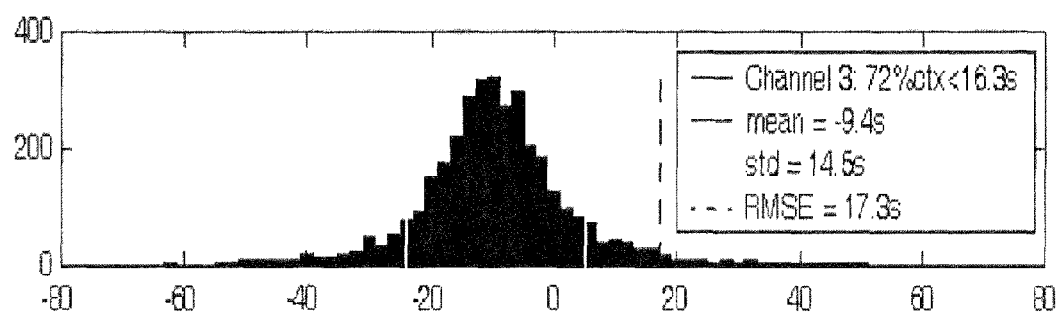
FIG. 3 is an illustration of the ability of an intra-uterine pressure catheter to detect a contraction early versus the method disclosed in the subject invention based on monitored EHG data.

FIG. 3 illustrates the ability of the maternal-fetal monitoring system to extract EHG method (in this example, a single channel) and detect most contractions earlier than the IUPC. In the maternal-fetal monitoring system's electrode, the mean contraction was detected 9.4 seconds ahead of the IUPC trace. The objective of this study was to align the EHG traces with the IUPC traces.

EXAMPLE 3

Estimating Contraction Onset

Figure 4A:
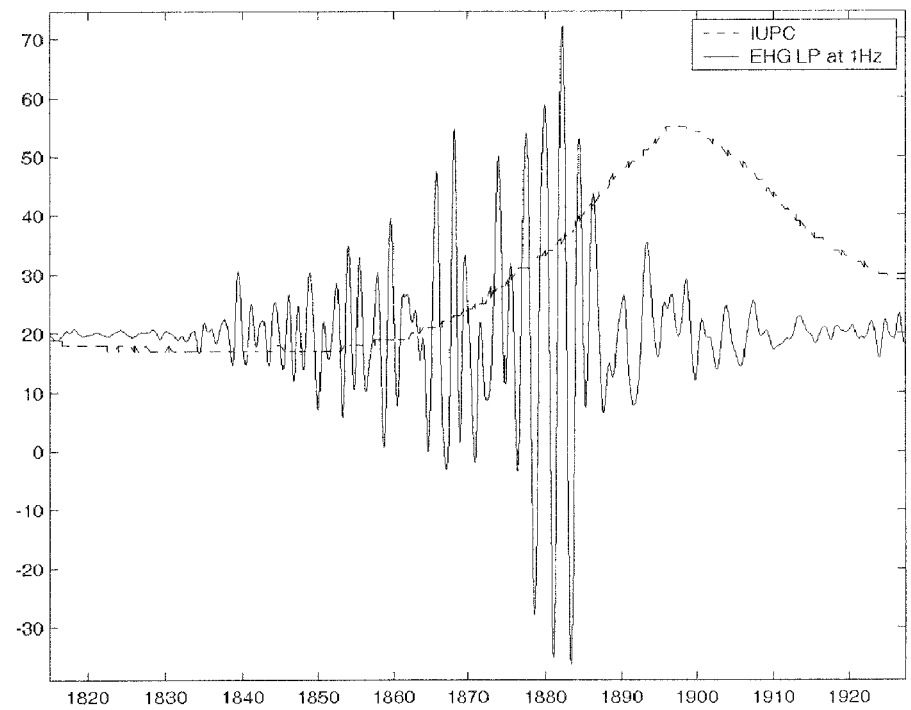
FIGS. 4A and 4B are additional illustrations of the ability of an intra-uterine pressure catheter to detect contractions early versus the method disclosed in the subject invention based on monitored EHG data.
Figure 4B:
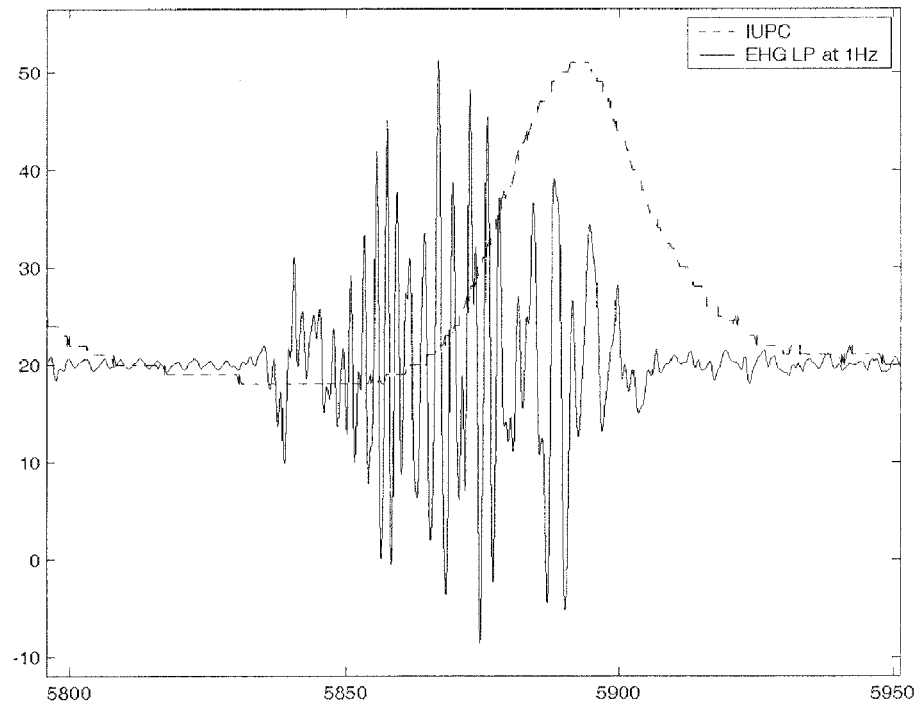

For predicting contraction onset, the unprocessed signal (prior to envelope detection described above) is preferably utilized as a basis since it preserves much more of the timing information of the original event. FIGS. 4A and 4B present two illustrative examples of the EHG extracted from a clinical study of the monitor conducted at the University of Florida's Shands Hospital (IRB #528-2003). In this study, the use of the monitoring system described herein for extracting EHG and ECG was investigated in term, laboring women who were simultaneously monitored with traditional electronic monitors, in this case with IUPC placed for obstetric indications. It can be observed from these examples that, indeed, the EHG signal precedes the increase in pressure measured by the IUPC.

In one embodiment, the obstetric analgesic system of the invention comprises a modeling and signal processing means to predict the occurrence of the contraction with sufficient lead-time to communicate this information to the user (e.g., the patient, the caregiver, etc.). Preferably, the information is communicated to the obstetric analgesic system to automatically activate the delivery of remifentanil, nitrous oxide, or another short-acting analgesic such that peak drug effect matches the peak of pain during contraction.

EHG Signal Processing

To predict the occurrence of a contraction, signal processing algorithms were derived to characterize the features of EHG data and to automatically detect them using a clinical data monitoring means in accordance with the subject invention.

A large database of EHG data from laboring women collected over the last several years (IRB 528-2003, n=500 to date) will be used to derive such algorithms and to assess their accuracy. Specifically, from this database, the EHG data will be extracted from women in labor with a pregnancy of $\geq 37$ weeks' gestation, who were simultaneously monitored with an IUPC for obstetric indications. These paired EHG and IUPC traces will be used to develop and test the new signal processing algorithms described below.

Characterization of the EHG Features

Preliminary results show that EHG has the potential to be the precursor for use in the subject invention to make a short-acting opioid, such as remifentanil, practical for pain management during labor. Indeed, where EHG is detected reliably at its onset, it can provide the time necessary for the drug to take effect. It is postulated that standard techniques based on power of the signal and thresholds are unlikely to provide the largest prediction time. Therefore, signal processing algorithms for rapid, real-time extraction of features in the EHG and detection of the onset of a contraction are preferred.

Examples of algorithms include time and frequency domain methods that minimize the latency for detection. Although the main characteristic of a contraction in the EHG signal is the increase in signal power (which suggests the use of envelope detectors), the smoothing and long response time disqualifies linear phase lowpass filters (e.g., moving average filters).

According to the subject invention, two other methods can be used to assess feasibility and accuracy. One method is based on the detection of the sudden increase in power in the instantaneous frequency of the EHG signal. The frequency of the oscillation is often unknown and it may change both among patients and even within a given patient from contraction to contraction. Therefore, a phase lock loop (PLL) detector centered at 1 Hz with a capture range of 0.25 Hz can provide excellent, low latency responses.

PLLs are well known devices utilized in all advanced forms of communication systems, and are well known for their fast response (Smith J. *Modern Communication Circuits*. McGraw-Hill, 1985). The output of the PLL's can be the envelope of the signal, but obtained with minimal delay through instantaneous demodulation. The limitation of the PLL is its capture range, i.e., the deviation between the input oscillatory EHG and the PLL center frequency that will still result in demodulation. The PLL can be an excellent method for the early detection of contractions.

Time series modeling (and in particular, linear prediction) is perhaps the fastest response system for time series analysis (Rabiner L, Schafer R. *Processing of Speech Signals*. Prentice Hall, 1978). The idea is to fit a predictor to an EHG signal without contraction, and monitor the prediction error. When the EHG signal changes toward a contraction, the error will increase suddenly. Theoretically, predictors take away the structure of the time series, producing an error that is white noise, and can be statistically evaluated for likelihood ratio tests (Fancourt C, Principe J. Nonlinear Dynamical Systems: feedforward neural network perspectives. John Wiley, 2000). This is the added advantage of the prediction methodology; it leads directly to the detection stage without further computation.

The issues in developing predictors for biological signals are reasonably well known: short models are preferred to allow for the inter- and intra-subject variability (Binnie C, Cooper R, Mauguir F. Clinical Neurophysiology. Elsevier, 2003). These theories can be applied to systems of the invention to design moving average (MA) models for both the background and the contraction. According to the subject invention, several exemplars of both segment types taken from several subjects can be collected from a study population. From these segments, MA models can be estimated using standard model fitting algorithms (Rabiner L, Schafer R. Processing of Speech Signals. Prentice Hall, 1978). The model order can then be determined by checking the whiteness of the error sequences using standard statistical procedures for time series modeling (Binnie C, Cooper R, Mauguir F. Clinical Neurophysiology. Elsevier, 2003). The output of the signal processing stage subsequently generates hypotheses for the detection stage.

Detection Stage

The output of the features (either the envelope of the PLL or the error sequences created by the background and the contraction predictors) can be tested for the occurrence of the contraction. The general framework of the design and specific details of each method are presented herein.

Two hypotheses are created: H0, the null hypothesis that the signal is background and H1 that a contraction started. The framework of generalized likelihood ratio tests (GLRT) are used due to their robustness and principled approach (Fancourt C, Principe J. Nonlinear Dynamical Systems: feedforward neural network perspectives. John Wiley, 2000).

GLRT is an extension of likelihood ratio tests of statistics, but modified to time series. This is accomplished by creating independent identically distributed (IID) variables from time series, which is achieved by destroying the time structure contained in the signal as done by predictors. An LRT is implemented as follows:

Let X(n) represent the history of a single realization (measurement) of a random process over n discrete time steps $$X(n) \equiv [x(n)x(n-1) \ldots x(1)]^\dagger$$

X(n) is assigned as belonging to one of K known random processes. A random process is completely characterized by its multi-variate distribution across time. Therefore, let $H_i$ be the hypothesis that the sequence belongs to the multi-variate distribution, $p_i(X)$ i=1 . . . K.

It is assumed that there are no costs associated with incorrect decisions and that no prior information is available about the relative occurrence of the various regimes. Let i* be the true process and let $i_*^\sim$ be the estimate of the true process. If a decision within $n_{max}$ time steps must be made, then the best decision is to choose the hypothesis based on the most likely sequence at time $n_{max}$ $$i^* = \mathrm{argmax}_i[p_i(X(n_{max}))]$$

If the goal is fast detection, at the expense of false alarms, then the multi-hypothesis sequential probability ratio test (SPRT) is appropriate. The log-likelihood ratio between any two candidate pdf s evaluated at the measured sequence is $$L_{ij}(n) = \log\left[\frac{p_i(X(n))}{p_j(X(n))}\right]$$

where $L_{ii}(n)$ is trivially zero. As can be easily shown, if i=i* is the true process, from information theory it is known that $L_{i*j}(n)$ will increase with time for all. The multi-hypothesis SPRT exploits this through a set of parallel Neyman-Pearson tests for deciding among the K hypotheses.

The performance of this test can be conducted using receiver operating characteristics (ROC) curves, i.e. a graph of the number of true detections can be constructed (i.e., true contractions) versus false detections (i.e., contractions predicted by the algorithm when they do not occur). For a clinically acceptable operating point, the number of false alarms created by each one of the feature extraction algorithms is accounted for to decide which is the best method and best threshold.

For the PLL detector, the GLRT has to be modified slightly. A single amplitude threshold is created from which a ROC curve is derived. Since the feature will not be white, a refractory period is created (given by the duration of the normal contraction) that will discard new detections once the threshold has been crossed.

Since the SPRT favors fast detection at the expense of false alarms, the detection algorithm of the subject invention can also exploit the quasi periodicity of the contractions. In fact, once a contraction occurs, there is a quieting period where the probably of a contraction is very low. This information can be incorporated in the detection algorithm as a time varying prior that will affect the threshold for the definition of a contraction.

In one embodiment, contractions are modeled as an inhomogeneous Poisson process, characterized by its conditional intensity function λ(t|x(t), θ(t), H(t)), which is defined as $$\lambda(t \mid x(t), \theta(t), H(t)) = \lim_{\Delta t \to 0} \frac{Pr(N(t + \Delta t) - N(t) = 1 \mid x(t), \theta(t), H(t))}{\Delta t} \quad (1)$$

where x(t) is the model system state, θ(t) is the parameter of the model, and H(t) is the history of all states, parameters and the discrete observations up to time t. The relationship between the only parameter in the Poisson process and the state x(t) and parameter θ(t) is represented by a nonlinear function $f(\cdot)$.

$$\lambda(t|x(t),\theta(t)) = f(x(t), \theta(t)) \quad (2)$$

The posterior density of the whole state vector x(t) at time $t_k$ given the spiking observation event $\Delta N_k$ (which is 0 or 1 during the time interval $(t_{k-1}, t_k]$) can be represented by Bayes rule as $$p(x_k|\Delta N_k, H_k) = \frac{p(\Delta N_k|x_k, H_k)p(x_k|H_k)}{p(\Delta N_k|H_k)} \quad (3)$$

where $p(\Delta N_k|x_k,H_k)$ is the probability of observing spikes $(t_{k-1}, t_k]$ defined by the Poisson process as $$Pr(\Delta N_k|x_k,H_k) = (\lambda(t_k|x_k, H_k)\Delta t)^{\Delta N_k} \exp(-\lambda(t_k|x_k, H_k)\Delta t) \quad (4)$$

and $p(x_k|H_k)$ is the one-step prediction density defined by Chapman-Kolmogorov equation as $$p(x_k|H_k) = \int p(x_k|x_{k-1}, H_k)p(x_{k-1}|\Delta N_{k-1}, H_{k-1})dx_{k-1} \quad (5)$$

where $x_k$ is generated by a linear state evolution:

$$x_k = F_k x_{k-1} + \eta_k \quad (6)$$

where $\eta_k$ is a zero-mean Gaussian white noise with covariance $Q_k$. By equation (4) and (5), the posterior density of the state $p(x_k|H_k)$ can be recursively estimated based on all the spike observations. This is a number (the prior probability of a contraction occurring at time $t_k$) that is multiplied by the output of the hypothesis testing block (the likelihood) created by the signal processing algorithms as explained above. The number of false alarms is then compared before and after this in a homogenous Poisson process.

For development of these algorithms, the retrospective data can be randomized into two equal groups. The first group of patients is used to develop and test the algorithms described above. Criteria for evaluation of the algorithms can include: the number of false alarms, the mean contraction prediction time (relative to current methods), and the standard deviation of the contraction prediction time.

EXAMPLE 4

Obstetric Remifentanil System

In one embodiment of the invention, a labor analgesic system is provided that coordinates delivery of a short-acting opioid, e.g., remifentanil, such that peak effectiveness of the analgesic coincides with episodic contraction-induced pain. In a particular embodiment, the obstetric analgesic system includes a reliable warning signal that detects the onset of a contraction 10-20 seconds, preferably 15 seconds, earlier than traditional uterine activity monitoring systems (such as a tocodynomometer or an IUPC).

Studies have found that remifentanil could provide adequate analgesia for labor and that relief is generally superior to meperidine, the most common i.v. opioid for labor. However, a greater decrease in peak Visual Analog Scale (VAS) pain scores is desirable. One limitation to remifentanil administration by traditional PCA is the difficulty in anticipating the onset of a uterine contraction.

There are two clinical tasks to be accomplished in accordance with the subject invention: assess how pain evolves during a contraction, from onset through recovery; and compare adequacy of analgesia with remifentanil PCA by standard use (based on patient recognition of contraction) versus when patients are provided an audible, visible, or tactile warning signal at the onset of a contraction as (1) detected by the uterine activity monitor (tocodynamometer or IUPC), (2) detected by EHG, (3) predicted by algorithms (e.g., using neural networks or other processing system) based on available contraction data (such as maternal or caregiver input, traditional, EHG, and the like).

According to the subject invention, a study can be performed on healthy women in labor with a pregnancy of ≧37 weeks' gestation, with no active medical or obstetric complications and a presumed healthy fetus in cephalic presentation, to assess the tasks described above. Patients that are: more than 6 cm dilated, have received an opioid analgesic in the last two hours, have a known hypersensitivity reaction to any opioid analgesic or have chronically used sedative or opiate agents, are excluded from the study. During anesthetic evaluation, all analgesic options are discussed including no analgesic intervention, standard i.v. opioids (such as nalbuphine or morphine), epidural/neuraxial anesthesia, and the study protocol with remifentanil. The patient can switch to any of the other analgesic options at any time.

For those patients who select remifentanil, informed consent is obtained. A three-way stopcock is interposed between the patient's i.v. tubing and the catheter hub on the existing i.v., thus minimizing dead-space between the infusion pump and the patient's circulation. In addition to the standard monitors (contraction, fetal heart rate, intermittent temperature), pulse oximetry (including maternal heart rate) are continuously monitored; respiratory rate and blood pressure are recorded at ten-minute intervals.

Figure 5:
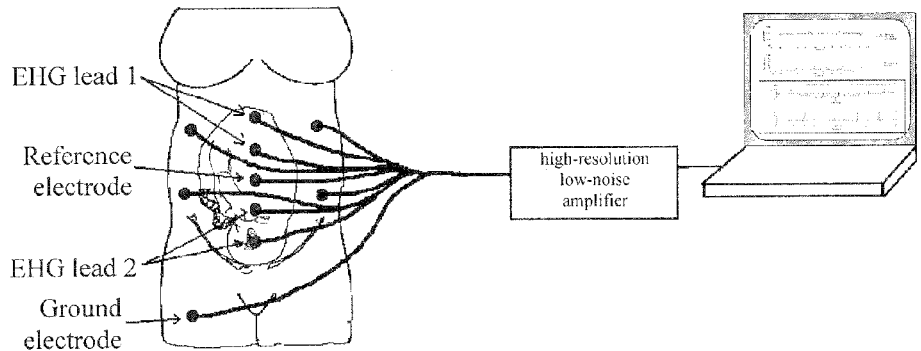
FIG. 5 is an illustration of one embodiment of an obstetric analgesia system of the invention that provides a signal at a specified time prior to the occurrence of a contraction.

Electrodes are applied to the patient's abdomen (using a monitoring system such as those disclosed in U.S. patent application Ser. No. 10/857,107 or an IUPC or tocodynamometer) and EHG data recorded for subsequent analysis using real-time data collection means. The existing monitoring system (as disclosed in U.S. patent application Ser. No. 10/857,107) is shown in FIG. 5 and includes the electrodes, a low-noise, high-gain amplifier, an analog to digital converter, and custom software (which include algorithms such as those described above) running on a computing means. The computing means processes the IUP or tocodynamometry signal or the selected algorithm and provides an audible (or visual or tactile) signal to the patient. The patient is instructed to depress the PCA button upon hearing this signal. The output of the PCA button is monitored by the computing means and stored in the database along with the system outputs and raw data from the electrodes. In certain embodiments, the computing means performs these steps automatically. In other embodiments, a trained anesthesia personnel is in attendance at all times.

Figure 6:
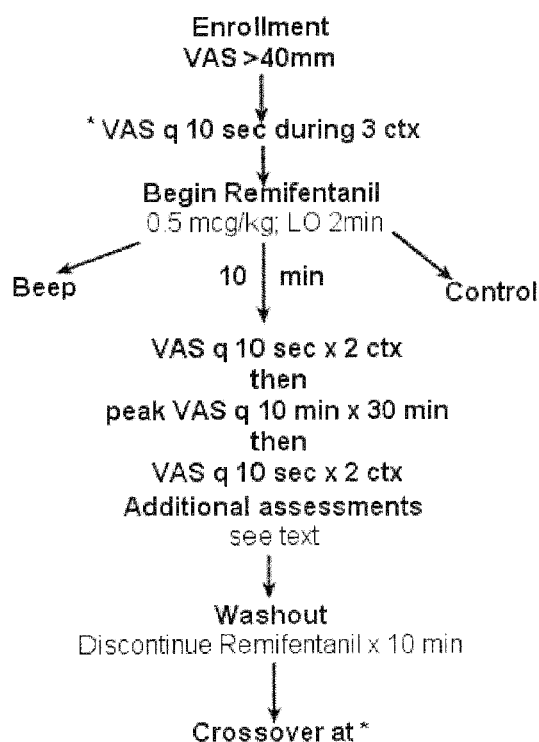
FIG. 6 is a flow diagram illustrating the steps involved in patient controlled administration of an analgesic when using an obstetric analgesia system of the invention.

Patients preferably begin the study protocol (FIG. 6) when their pain during a contraction exceeds 40 on a 100 mm VAS. When notified by the nurse, the user first evaluates the evolution of the VAS over three contractions by having the patient mark the scale at 10-second intervals. Simultaneously, the user obtains baseline assessments of nausea, itching and sedation (0=none, 1=mild, 2=moderate, 3=severe), and fetal heart rate variability (0=absent, 1=reduced, 2=average, 3=exaggerated). A randomized assignment schedule is used to determine whether the patient begins with the auditory reminder (Beep) or with traditional PCA (Control).

The user can begin a remifentanil PCA at 0.5 mcg/kg with a 2-minute lockout, and instruct the patient to press the button either at the onset of a contraction, "the earlier the better" (Control), or at the sound of the beep (Beep). After 10-minutes, VAS is assessed at 10-second intervals for two contractions, then only the peak VAS is noted every 10-minutes for a total of 30-minutes. The VAS for the next two contractions is assessed at 10-second intervals. In addition to recording the total amount of drug used, subjects are asked to rank pain relief (4=complete, 3=good, 2=moderate, 1=slight, 0=no relief), and grade side effects (nausea, itching, sedation) with verbal scales. The CTG will also be scored. The remifentanil is then disabled for a 10-minute washout period.

The user can then switch the patient to the other arm of the study (Control or Beep), and explain the new methodology for activating the PCA. The same protocol is repeated for another 30-minutes.

Upon completion of the study (just over one hour), patient satisfaction is assessed, as well as whether the subject would be interested in continuing with remifentanil, were it available. After delivery, Apgar scores at one and five minutes, umbilical cord blood gases, and neonatal resuscitation are recorded, together with subsequent maternal analgesics and circumstances of delivery.

Safety

Trained anesthesia personnel are preferably in attendance throughout the protocol. To avoid hypoxemia, supplemental oxygen is administered whenever the SpO2 falls below 95% for more than 15 seconds. The remifentanil PCA bolus is decreased in the presence of any one or combination of the following:

Respiratory rate<8 breaths/min
SpO2<90% for >15 seconds
MAP (mean arterial pressure)<75% baseline
Maternal heart rate<50 bpm
Fetal heart rate sustained<110 bpm
Sedation score>2

If any of these adverse events persists, the study is stopped and appropriate intervention provided. The study can also be terminated at patient request.

Statistical Analysis

Because pain intensity increases during labor, the mean of the pain scores given before each study arm can be used as the reference value for that study arm, and a pain intensity difference calculated. A Mann-Whitney U test is applied to ensure there was no period effect or treatment-period interaction. Statistical analysis is performed in consultation with a biostatistician at the University of Florida, applying Mann-Whitney U, unpaired t-tests, or $\chi^2$-tests as appropriate to compare quality of analgesia and severity of side-effects.

EXAMPLE 5

Effectiveness of Obstetric Analgesic System

In this study, the effect of a patient trigger for contraction onset based on the EHG signal, on the quality of i.v. remifentanil labor analgesia, is assessed.

Using the signal processing tasks described herein, an appropriate algorithm is applied to EHG data to established a time for providing a warning signal to the user. The timing of the EHG-derived warning signal is then compared with the actual PCA activation for each group (Control and Beep) using repeated measures ANOVA.

The study is repeated comparing the better of the two regimens identified in the study of Example 4, with the use of an audible warning signal triggered by the EHG-detected onset of a contraction. The same crossover design and statistical analysis are repeated.

In the next phase, efforts to further improve the analgesia achieved with remifentanil can include (1) supplementation with an NMDA-receptor antagonist, which may prevent tolerance to remifentanil, and/or (2) supplementation with nitrous oxide, also triggered by the anticipated contraction onset. The user can close the loop and enable automatic administration of remifentanil without requiring maternal input, though she would retain the ability to increase or decrease the bolus dose. For safety, the system of the invention receives data including maternal pulse oximetry, heart rate, and perhaps fetal heart rate (as obtained by the electrode array or via standard monitors). It is an object of this study to provide a self-contained maternal labor analgesia system that is superior to those techniques currently available to those who cannot or choose not to receive a neuraxial anesthetic.

EXAMPLE 6

Estimating Contraction Onset in Morbidly Obese Patients

As described above, labor contractions are typically monitored with a strain gauge (tocodynamometer (toco)), providing frequency and approximate duration. In obese patients, the distance from the skin to the uterus may be such that the toco does not reliably detect contractions. In this setting, or when quantitative measure of intrauterine pressure (IUP) is deemed necessary, an invasive IUPC is required. This study compared EHG-derived contractions estimated using the systems and methods of the invention as compared with both toco and IUP monitoring in morbidly obese laboring women.

Methods

A system comprising signal processing hardware to non-invasively extract the fetal ECG and EHG was devised in accordance with the subject invention. After written, informed consent and skin preparation, an array of eight 3-cm$^2$ Ag/AgCl$_2$ electrodes was placed over the maternal abdomen and signals amplified with high gain, low noise amplifiers. All signals were measured with respect to a reference electrode, with driven right leg circuitry to reduce common mode noise. The amplifier 3 dB bandwidth is 0.1 Hz and 100 Hz, with a 60 Hz notch. The contraction location is derived by downsampling the signal at 20 Hz, filtering at 0.015 Hz (EHG) or 0.03 Hz (IUP/toco), then low pass filtering at 0.003 Hz for threshold purposes. Contractions are rejected if: duration <30 s or >120 s, amplitude <30% of median of last 10 contractions; for toco/IUP, a minimum amplitude of 5 units is also applied. The contraction correlation index was reported as $(CCI)^{(1)}=\#$ consistent ctx/½[(# IUP or toco-ctx)+(# EHG-ctx)].

This study evaluated data from 14 laboring subjects with BMI=34 who had an IUPC placed during EHG monitoring. 30-minute segments were selected before and after placement.

Results

Of the 14 patients (BMI 45.1±7.9), 6 underwent AROM at the time of IUPC placement. Toco identified 155 vs 195 EHG-contractions, while IUP identified 192 vs 185 EHG-ctx. CCI was 0.79±0.29 vs 0.92±0.12 for toco and IUP, respectively.

Discussion

Contraction monitoring is routinely employed for managing labor. Non-invasive monitoring is preferable, but toco may be unreliable in morbidly obese patients. The EHG-derived contraction pattern was relatively consistent through the study period, while in some cases the toco registered very few contractions. EHG as monitored using the systems and methods of the invention correlated much better with IUP than with toco, exceeding 90% in 13/14 patients. Accordingly, the subject systems and methods that assess EHG to estimate contraction onset provides a non-invasive means of monitoring labor, particularly for those in whom toco is inadequate.

All patents, patent applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A maternal labor pain management system comprising:
a) at least one analgesic pain management means;
b) a system for administering the pain management means, wherein the system for administering the pain management means is a patient controlled system; and
c) a system for analyzing uterine activity in the prediction of labor contractions to predict time of contraction onset relevant for use in coordinating the administration of the pain management means, wherein the system for analyzing uterine activity provides at least one signal regarding the predicted time of contraction onset and wherein the system for analyzing uterine activity is operably connected to the system for administering the pain management means, wherein the system for analyzing uterine activity comprises:
 i) at least two abdominal electrode sensors to receive a mixture of maternal and fetal vital signals; and
 ii) a computing means for analyzing the mixture of maternal and fetal vital signals from the sensors, said computing means including hardware and software, wherein said software comprises a function to extract electrohysterogram (EHG) data from the maternal and fetal vital signals for use in determining the predicted time of contraction onset, and
wherein the system for administering the pain management means is responsive to the predicted time of contraction onset determined by the computing means to automatically initiate and cease the delivery of the analgesic pain management means.

2. The maternal labor pain management system of claim 1, wherein at least two pain management means are provided.

3. The maternal labor pain management system of claim 2, wherein the pain management means is selected from the group consisting of: analgesics, anesthetics, sedatives, tranquilizers, narcotic antagonist combinations, and electrical stimulation devices.

4. The maternal labor pain management system of claim 1, wherein the signal(s) regarding the predicted time of contraction onset is provided audibly, visibly or tactilely.

5. The maternal labor pain management system of claim 1, wherein the system for analyzing uterine activity further includes, in addition to the abdominal electrodes, any one or more sensor selected from the group consisting of: maternal sensation, an intrauterine pressure catheter, a tocodynamometer, and a uterine electromyogram.

6. A method for administering an analgesic to an obstetric patient, where said method comprises:
a) utilizing a maternal labor pain management system comprising:
 1) at least one analgesic pain management means;
 2) a system for administering the pain management means; and
 3) a system for analyzing uterine activity in the prediction of labor contractions to predict time of contraction onset relevant for use in coordinating the administration of the pain management means, wherein the system for analyzing uterine activity provides at least one signal regarding the predicted time of contraction onset and wherein the system for analyzing uterine activity is operably connected to the system for administering the pain management means, wherein the system for analyzing uterine activity comprises:
  i) at least two abdominal electrode sensors to receive maternal and fetal signals; and
  ii) a computing means for analyzing the maternal and fetal signals from the sensors, said computing means including hardware and software, wherein said software comprises a function to extract electrohysterogram (EHG) data from the maternal and fetal signals for use in determining the predicted time of contraction onset, and
wherein the system for administering the pain management means is responsive to the predicted time of contraction onset determined by the computing means to automatically initiate and cease the delivery of the analgesic pain management means, and
b) receiving into the computing means signals received by the abdominal electrode sensors;
c) implementing the computing means, without clinician input, to evaluate the signals to determine the predicted time of contraction onset; and
d) recommending, without clinician input, a time for administering the analgesic pain management means based on the predicted time of contraction onset, wherein said administration time is appropriate for the patient at that particular contraction.

7. The method of claim 6, further comprising the step of automatically delivering the analgesic pain management means to the patient based on the recomrnendation derived from step (d).

8. The method of claim 6, wherein the system for administering the pain management means further includes a gas mixing valve for a volatile anesthetic or gas.

9. The method of claim 8, wherein the volatile gas is nitrous oxide.

10. The method of claim 6, wherein the analgesic pain management means is an intravenous analgesic.

11. The method of claim 10 wherein the analgesic is Remifentanil.

12. The method of claim 6, further comprising the step of signaling the appropriate time for administering the analgesic pain management means to the patient.

13. The method of claim 12, wherein the signal is selected from the group consisting of: an audible signal, a visible signal, and a tactile signal.

14. The method of claim 6, wherein the system for analyzing uterine activity includes, in addition to the abdominal sensors, any one or more sensors selected from the group consisting of: maternal sensation, an intrauterine pressure catheter, a tocodynamometer, and a uterine electromyogram, to receive maternal and fetal signals.

15. The method of claim 6, wherein the computing means further comprises a neural network.

16. The method of claim 6, further comprising the step of administering electrical stimulation.

17. A maternal labor pain management system comprising:
a) at least one analgesic pain management means having a pain-relieving ability;
b) a system for administering the pain management means; and
c) a system for analyzing uterine activity in the prediction of labor contractions to predict any one or more of the following contraction data selected from the group consisting of:
contraction frequency, contraction duration, contraction intensity, time of history of contractions, and extent and/or intensity of contraction-induced pain that is relevant for use in coordinating the administration of the pain management means, wherein the system for analyzing uterine activity provides at least one contraction data signal and wherein the system for analyzing uterine activity is operably connected to the system for administering the pain management means, wherein the system for analyzing uterine activity comprises:
  i) at least two abdominal electrode sensors to receive a mixture of maternal and fetal vital signals; and
  ii) a computing means for analyzing the mixture of maternal and fetal vital signals from the sensors, said computing means including hardware and software, wherein said software comprises a function to extract electrohysterogram (EHG) data from the maternal and fetal vital signals for use in predicting contraction data, and
wherein the system for administering the pain management means is responsive to the predicted contraction data signal to automatically initiate and cease the delivery of the analgesic pain management means such that the pain relieving ability of the analgesic coincides with the predicted contraction data.

18. The maternal labor pain management system of claim 17, wherein the system for administering the pain management means is responsive to the signal regarding the predicted extent and/or intensity of contraction-induced pain to automatically initiate and cease the delivery of the analgesic pain management means such that the pain-relieving ability of the analgesic pain management means coincides with the extent and/or intensity of contraction-induced pain.

19. The maternal labor pain management system of claim 17, further comprising a pulse oximeter and/or a respiratory rate monitoring apparatus.

20. The maternal labor pain management system of claim 17, further comprising an automated shut-off feature for shutting off the delivery of the analgesic pain management means should detrimental effects from the delivery of the analgesic pain management means be exhibited.

21. The maternal labor pain management system of claim 17, further comprising an automated feature for increasing inspired oxygen concentration following exhibited detrimental effects from the delivery of the analgesic pain management means.

22. The maternal labor pain management system of claim 17, wherein the system for analyzing uterine activity comprises at least 8 abdominal electrode sensors.

* * * * *

UNITED STATES PATENT AND TRADEMARK OFFICE
CERTIFICATE OF CORRECTION

PATENT NO. : 8,211,015 B2
APPLICATION NO. : 12/986520
DATED : July 3, 2012
INVENTOR(S) : Tammy Y. Euliano et al.

It is certified that error appears in the above-identified patent and that said Letters Patent is hereby corrected as shown below:

Column 10,
Line 60, "moderns" should read --modems--

Column 23,
Line 47, "deter mining" should read --determining--

Column 28,
Line 40, "n=500" should read --n≥500--

Column 28,
Lines 43-44, "≧37 weeks'" should read --≥ 37 weeks'--

Column 29,
Line 56, "HO" should read --H0--

Column 30,
Line 14, "i.~" should read -- $\tilde{i}_*$ --

Column 30,
Line 19, " $i^*=\text{argmax}_i[p_i(X(n_{max}))]$ " should read -- $\tilde{i}* = \text{argmax}_i[p_i(X(n_{max}))]$ --

Column 30,
Line 23, "pdf s evaluated" should read --pdf's evaluated--

Column 31,
Line 1, "Poisson process and the" should read --Poisson process λ and the--

Signed and Sealed this
Ninth Day of October, 2012

David J. Kappos
*Director of the United States Patent and Trademark Office*

CERTIFICATE OF CORRECTION (continued)
U.S. Pat. No. 8,211,015 B2

Column 32,

Lines 9-10, "$\geqq$ 37 weeks'" should read --$\geq$ 37 weeks'--

Column 34,

Line 49, "BMI = 34" should read --BMI $\geq$ 34--